United States Patent
Dobak et al.

(10) Patent No.: US 9,597,531 B2
(45) Date of Patent: Mar. 21, 2017

(54) SELECTIVE, LIPOPHILIC, AND LONG-ACTING BETA AGONIST MONOTHERAPEUTIC FORMULATIONS AND METHODS FOR THE COSMETIC TREATMENT OF ADIPOSITY AND CONTOUR BULGING

(75) Inventors: John Daniel Dobak, La Jolla, CA (US); Kenneth Walter Locke, Carlsbad, CA (US)

(73) Assignee: NEOTHETICS, INC., San Diego, CA (US)

( * ) Notice: Subject to any disclaimer, the term of this patent is extended or adjusted under 35 U.S.C. 154(b) by 938 days.

(21) Appl. No.: 13/303,045

(22) Filed: Nov. 22, 2011

(65) Prior Publication Data

US 2012/0178819 A1 Jul. 12, 2012

Related U.S. Application Data

(60) Provisional application No. 61/417,098, filed on Nov. 24, 2010.

(51) Int. Cl.
| | |
|---|---|
| A01N 43/00 | (2006.01) |
| A61K 31/33 | (2006.01) |
| A01N 37/18 | (2006.01) |
| A61K 31/16 | (2006.01) |
| A61Q 19/06 | (2006.01) |
| A61K 8/41 | (2006.01) |
| A61K 9/00 | (2006.01) |
| A61K 9/19 | (2006.01) |
| A61K 31/137 | (2006.01) |
| A61K 31/138 | (2006.01) |
| A61K 47/10 | (2006.01) |
| A61K 47/34 | (2006.01) |

(52) U.S. Cl.
CPC ........... *A61Q 19/06* (2013.01); *A61K 8/41* (2013.01); *A61K 9/0019* (2013.01); *A61K 9/19* (2013.01); *A61K 31/137* (2013.01); *A61K 31/138* (2013.01); *A61K 47/10* (2013.01); *A61K 47/34* (2013.01); *A61K 2800/91* (2013.01)

(58) Field of Classification Search
CPC .......... A61K 2800/91; A61K 31/137; A61K 31/138; A61K 47/10; A61K 47/34; A61K 8/41; A61K 9/0019; A61K 9/19; A61Q 19/06
USPC .................................. 514/629, 651
See application file for complete search history.

(56) References Cited

U.S. PATENT DOCUMENTS

| | | | |
|---|---|---|---|
| 4,525,359 A | 6/1985 | Greenway et al. | |
| 4,800,079 A | 1/1989 | Boyer | |
| 4,826,879 A | 5/1989 | Yamamoto et al. | |
| 5,126,147 A | 6/1992 | Silvestri et al. | |
| 5,270,305 A | 12/1993 | Palmer | |
| 5,314,916 A | 5/1994 | York et al. | |
| 5,496,803 A | 3/1996 | Meier et al. | |
| 5,709,884 A | 1/1998 | Trofast et al. | |
| 5,855,913 A | 1/1999 | Hanes et al. | |
| 5,919,827 A | 7/1999 | Barberich et al. | |
| 5,972,919 A | 10/1999 | Carling | |
| 6,030,604 A | 2/2000 | Trofast | |
| 6,066,675 A | 5/2000 | Wen et al. | |
| 6,110,974 A | 8/2000 | Aberg et al. | |
| 6,316,443 B1 | 11/2001 | Baldwin et al. | |
| 6,384,259 B1 | 5/2002 | Stogniew et al. | |
| 6,537,983 B1 | 3/2003 | Biggadike et al. | |
| 6,643,212 B1 | 11/2003 | Jones, Jr. et al. | |
| 6,656,508 B2 | 12/2003 | Goldenberg et al. | |
| 6,869,942 B2 | 3/2005 | Trofast et al. | |
| 7,172,752 B2 | 2/2007 | Watanabe et al. | |
| 7,253,156 B2 | 8/2007 | Currie et al. | |
| 7,267,813 B2 | 9/2007 | Watanabe et al. | |
| 7,348,362 B2 | 3/2008 | Banerjee et al. | |
| 7,354,913 B2 | 4/2008 | Trofast et al. | |
| 7,638,508 B2 | 12/2009 | Biggadike et al. | |
| 7,662,815 B2 | 2/2010 | McKinnell et al. | |
| 7,723,392 B2 | 5/2010 | Aberg et al. | |
| 7,829,554 B2 | 11/2010 | Dobak | |
| 8,404,750 B2 | 3/2013 | Dobak et al. | |
| 8,420,625 B2 | 4/2013 | Dobak | |
| 2002/0032149 A1 | 3/2002 | Kensey | |
| 2002/0042404 A1 | 4/2002 | Bauer | |

(Continued)

FOREIGN PATENT DOCUMENTS

| | | |
|---|---|---|
| CA | 2500065 | 5/2004 |
| CA | 2588168 | 6/2006 |

(Continued)

OTHER PUBLICATIONS

Nema et al. (Encyclopedia of Pharmaceutical Technology, 2007, p. 1622-1645).*
AU2007313077 Exam Report dated Jan. 29, 2010.
AU2007313077 Exam Report dated Oct. 13, 2010.
AU2010253864 Examiner's Report dated Sep. 17, 2013.
AU2007325523 Examination Report dated Mar. 24, 2010.
Ball et al. (1991) Salmeterol, a novel, long-acting beta 2-adrenoceptor agonist: characterization of pharmacological activity in vitro and in vivo. Br. J. Pharmacol. 104, 665-671.
Bray et al, Current and Potential Drugs for Treatment of Obesity, Endocrine Reviews, 20(6):805-875 1999.

(Continued)

*Primary Examiner* — Uma Ramachandran
(74) *Attorney, Agent, or Firm* — Wilson, Sonsini, Goodrich & Rosati

(57) ABSTRACT

Provided herein are pharmaceutical and cosmetic formulations and methods for regional adiposity reduction and treatment of body contour defects such as abdominal bulging; comprising an injectable formulation, said formulation comprising: an active ingredient that consists essentially of an adipose tissue-reducing amount of one or more lipophilic long-acting selective beta-2 adrenergic receptor agonists, or salts, solvates, or polymorphs thereof; and one or more subcutaneously acceptable inactive ingredients.

15 Claims, 2 Drawing Sheets

(56) References Cited

U.S. PATENT DOCUMENTS

| | | | |
|---|---|---|---|
| 2003/0022856 A1 | 1/2003 | Richardson et al. |
| 2003/0022911 A1 | 1/2003 | Smith et al. |
| 2003/0095925 A1 | 5/2003 | Dugger |
| 2003/0161207 A1 | 8/2003 | Jones, Jr. et al. |
| 2003/0236238 A1 | 12/2003 | Trofast et al. |
| 2004/0037875 A1 | 2/2004 | Metselaar et al. |
| 2004/0043032 A1 | 3/2004 | McKenzie et al. |
| 2004/0065325 A1 | 4/2004 | Trofast et al. |
| 2004/0171597 A1 | 9/2004 | Biggadike et al. |
| 2004/0208833 A1 | 10/2004 | Hovey et al. |
| 2004/0208910 A1 | 10/2004 | Ashton et al. |
| 2004/0209850 A1 | 10/2004 | Babul |
| 2004/0235922 A1 | 11/2004 | Baile et al. |
| 2004/0247628 A1 | 12/2004 | Lintz et al. |
| 2005/0048127 A1 | 3/2005 | Brown et al. |
| 2005/0069591 A1 | 3/2005 | Bernstein et al. |
| 2005/0075900 A1 | 4/2005 | Arguimbau |
| 2005/0113456 A1 | 5/2005 | Aberg |
| 2005/0141293 A1 | 6/2005 | Ha |
| 2005/0207989 A1 | 9/2005 | Trofast et al. |
| 2005/0222108 A1 | 10/2005 | Bhatarah et al. |
| 2005/0244339 A1 | 11/2005 | Jauernig et al. |
| 2005/0267080 A1 | 12/2005 | Kolodney et al. |
| 2006/0051299 A1 | 3/2006 | Chaudry |
| 2006/0188579 A1 | 8/2006 | Rogueda |
| 2006/0189587 A9 | 8/2006 | Bauer |
| 2007/0014843 A1 | 1/2007 | Dobak |
| 2007/0178051 A1 | 8/2007 | Pruitt |
| 2007/0178166 A1 | 8/2007 | Bernstein et al. |
| 2008/0157409 A1 | 7/2008 | Reens |
| 2008/0249017 A1 | 10/2008 | Loughrey et al. |
| 2008/0270175 A1 | 10/2008 | Rodriguez et al. |
| 2008/0300229 A1 | 12/2008 | Willcox et al. |
| 2009/0123550 A1 | 5/2009 | Phillips |
| 2010/0093693 A1 | 4/2010 | Shen et al. |
| 2010/0119609 A1 | 5/2010 | Dobak |
| 2010/0137267 A1 | 6/2010 | Dobak |
| 2010/0215710 A1 | 8/2010 | Isseroff et al. |
| 2011/0105446 A1 | 5/2011 | Dobak |
| 2011/0130373 A1 | 6/2011 | Dobak et al. |
| 2011/0166202 A1 | 7/2011 | Banerjee |
| 2011/0224176 A1 | 9/2011 | Dobak et al. |
| 2012/0015918 A1 | 1/2012 | Dobak |
| 2012/0046256 A1 | 2/2012 | Dobak |
| 2012/0046257 A1 | 2/2012 | Dobak et al. |
| 2014/0322305 A1 | 10/2014 | Dobak et al. |
| 2015/0328146 A1 | 11/2015 | Dobak et al. |

FOREIGN PATENT DOCUMENTS

| | | |
|---|---|---|
| CA | 2615173 | 1/2007 |
| CA | 2628178 | 5/2007 |
| CA | 2631493 | 6/2007 |
| CA | 2640444 | 8/2007 |
| CA | 2665564 | 6/2008 |
| CN | 1706501 | 12/2005 |
| EP | 0120165 | 7/1990 |
| EP | 1153614 | 11/2001 |
| EP | 1867334 | 12/2007 |
| GB | 1471326 | 4/1977 |
| GB | 2443287 | 4/2008 |
| GB | 2453188 | 4/2009 |
| GB | 2470818 | 12/2010 |
| GB | 2477030 | 7/2011 |
| JP | 59-155313 | 9/1984 |
| JP | 61-31043 | 2/1986 |
| JP | S61246129 A | 11/1986 |
| JP | 11106334 | 4/1999 |
| JP | H11507936 A | 7/1999 |
| JP | 2004-513340 | 4/2004 |
| JP | 2005-508220 | 3/2005 |
| JP | 2010525044 A | 7/2010 |
| KR | 2008-0067705 | 7/2008 |
| KR | 20080067705 A | 7/2008 |
| WO | WO-9812228 A1 | 3/1998 |
| WO | WO-98-41232 | 9/1998 |
| WO | WO 98/48810 | 11/1998 |
| WO | WO 01/19373 | 3/2001 |
| WO | WO 01/28535 | 4/2001 |
| WO | WO 03/033000 | 4/2003 |
| WO | WO 2004/028545 | 4/2004 |
| WO | WO-2004030659 A1 | 4/2004 |
| WO | WO 2004/091574 | 10/2004 |
| WO | WO 2004/103057 | 12/2004 |
| WO | WO 2004/103379 | 12/2004 |
| WO | WO-2005-007145 | 1/2005 |
| WO | WO 2005/007145 | 1/2005 |
| WO | WO 2005/072745 | 8/2005 |
| WO | WO 2006/122165 | 11/2006 |
| WO | WO 2007/011743 | 1/2007 |
| WO | WO-2007-117661 | 10/2007 |
| WO | WO-2008-048770 | 4/2008 |
| WO | WO-2008-066775 | 6/2008 |
| WO | WO-2008-067060 | 6/2008 |
| WO | WO-2008-157409 | 12/2008 |
| WO | WO-2009-000473 | 12/2008 |
| WO | WO-2010-138770 | 12/2010 |
| WO | WO-2011-088413 | 7/2011 |

OTHER PUBLICATIONS

CA 2,615,173 Examination Report dated Mar. 31, 2011.
CA 2,615,173 Examination Report dated Sep. 21, 2010.
CA 2,666,612 Office Action dated Nov. 9, 2010.
CA 2,761,744 Examination Report dated Oct. 9, 2013.
CA 2,666,564 Examination Report dated Oct. 19, 2010.
CN0780046201.3 Office Action dated Oct. 11, 2010 (w/English Translation).
CN200680031397.4 Office Action dated Dec. 27, 2013 (w/English Translation).
CN200780046741.1 Office Action dated Dec. 3, 2013 (w/English translation).
CN200780046741.1 Office Action dates Feb. 23, 2011 (w/English translation).
CN201080023277.6 Office Action dated Oct. 15, 2013 (w/English Translation).
Ding et al, Modulation of porcine adipocyte beta-adrenergic receptos by a beta-adrenergic agonist, J. of Animal Science, Apr. 2000, 78(4):919-926.
Djurhuus et al. (2002). Effects of cortisol on lipolysis and regional interstitial glycerol levels in humans. American Journal of Physiology—Endocrinology and Metabolism 283, E172-E177.
EP06787329.9 Office Action dated May 26, 2011.
EP07843370.3 Office Action dated Jan. 14, 2011.
EP07843370.3 Office Action dated Mar. 27, 2012.
EP07843370.3 Office Action dated Sep. 19, 2011.
EP07871172.8 Exam Report dated Sep. 8, 2010.
EP11180982.8 Exam Report dated Oct. 16, 2013.
EP1921919 B1 Opposition to a European patent dated Jun. 15, 2012.
GB0804401.8 Examination Report dated Aug. 21, 2009.
GB1008885.4 Exam Report dated Jul. 26, 2011.
GB1008885.4 Exam Report dated Sep. 19, 2012.
GB1120090.4 Office Action dated Nov. 29, 2013.
GB1207749.1 Exam Report dated Sep. 25, 2013.
Harrison (2004). Excerpt from www.macleans.ca online forum, article dated Feb. 25, 2004: "Love handles can be shrunk without surgery".
IL198184 Office Action dated Apr. 22, 2010 (English translation only).
Jensen (1997). Lipolysis: contribution from regional fat. Annu. Rev. Nut. 17, 127-139.
Johnson, M., "Pharmacology of long-acting β-agonists," Annals of Allergy Asthma & Immunology: Official Publication of the American College of Allergy, Asthma & Immunology, Aug. 1995, vol. 75, No. 2, pp. 177-179, ISSN: 1081-1206.
JP2009-234928 Office Action dated Nov. 1, 2010 (w/English Translation).
JP2008-521646 Office Action dated Jan. 4, 2011 (English Translation only).

(56) References Cited

OTHER PUBLICATIONS

JP2009-533423 Office Action dated Nov. 16, 2010 (w/English translation).
JP2011083171 Office Action dated Aug. 30, 2013 (w/ English Translation).
JP2012-095792 Office Action dated Sep. 10, 2013 (English translation only).
JP2012-513273 Office action dated Oct. 29, 2013 (w/English Translation).
Kiri et al. Inhaled corticosteroids are more effective in COPD patients when used with LABA than with SABA. Respir Med. Sep. 2005;99(9):1115-1124.
KR-10-2009-7009972 Office Action dated Aug. 22, 2011 (w/English translation).
KR-10-2012-7021302 Office action dated Nov. 19, 2013 (w/English translation).
KR-2009-7009974 Office Action dated Dec. 6, 2010 (w/English translation).
KR-2009-7009974 Office Action dated Jun. 1, 2011 (w/English translation).
Lamberts et al. (1975). The mechanism of the potentiating effect of glucocorticoids on catecholamine-induced lipolysis. Metabolism 24(6), 681-689.
Linden et al. (1996). Pharmacological basis for duration of effect: formoterol and salmeterol versus short-acting beta 2-adrenoceptor agonists. Lung 174, 1-22.
Mak et al. (1995). Glucocorticosteroids increase beta 2-adrenergic receptor transcription in human lung. American Journal of Physiology 268, L41-L46.
MX/a/2011/012542 office action dated Nov. 15, 2013 (w/English Translation).
Naline et al. (1994). Relaxant effects and durations of action of formoterol and salmeterol on the isolated human bronchus. European Respiratory Journal 7, 914-920.
PCT/US2006/027405 International Preliminary Report on Patentability date Jan. 16, 2008.
PCT/US2007/079740 International Preliminary Report on Patentability date Apr. 22, 2009.
PCT/US2007/081568 International Preliminary Report on Patentability date Apr. 22, 2009.
PCT/US2011/061973 International Search Report dated Dec. 28, 2012.
SG 201108652-7 Search Report dated Nov. 6, 2013 (English translation only).
SG201205142-1 Search Report and Written Opinion dated Oct. 29, 2013 (English Translation only).
Tomioka, K. et al., "Effects of Formoterol (BD 40A), a β-Adrenocepto Stimulant, on Isolated Guinea-Pig Ling Parenchymal Strips and Antigen-Induced SRS-A Release in Rats," Archives Internationales De Pharmacodynamie Et De Therapie, Jan. 1984, vol. 267, No. 1, pp. 91-102: ISSN:0003-9780.
U.S. Appl. No. 12/445,570 Office action dated Dec. 26, 2013.
U.S. Appl. No. 13/007,518 Office Action dated Jan. 24, 2014.
U.S. Appl. No. 13/204,423 Office Action dated Dec. 13, 2013.
Yang, et al. "Multiple actions of β-adrenergic agonists on skeletal muscle and adipose tissue." Biochem. J. (1989) 261, 1-10.
FDA 2002, pp. 1-2 (Update on Illegal Compounding of Clenbuterol Veterinary Drug Products).
Mamani-Matsuda et al., Long-acting beta2-adrenergic formoterol and salmeterol induce the apoptosis of B-Chronic lymphocytic leukemia cells, BR J. Haematol. Jan. 2004;124(2), printed from http://www.ncbi.nlm.nih.gov/pubmed/14687023, Abstract only, 2 pages.
McRea et al., "Salmeterol, a long-acting beta 2-adrenoceptor agonist mediating cyclic AMP accumulation in a neuronal cell line," Br. J. Pharmacol. Oct. 1993;110(2), printed from http://www.ncbi.nlm.nih.gov/pubmed/7902176, Abstract only, 2 pages.
Sato et al., "Prediction for effectiveness of steroid pulse therapy in the orbits of patients with Graves' ophthalmopathy," Nihon Naibunpi Gakkai Zasshi. Mar. 20, 1992;68(3), printed from http://www.ncbi.nlm.nih.gov/pubmed/1582520, Abstract only, 2 pages.
AU 2010253864 First Examiner's Report dated Jun. 15, 2012.
GB 1207749 Exam Report dated May 15, 2012.
GB 1008885.4 Exam Report dated Jul. 31, 2012.
KR 10-2009-70099772 Office Action dated Apr. 25, 2012 (English translation).
PCT/US2011/061972 Search report dated Jun. 15, 2012.
PCT/US2011/021424 International Preliminary Report on Patentability and Written Opinion dated Jul. 17, 2012.
PCT/US06/027405 Search rpt mailed Aug. 28, 2007.
U.S. Appl. No. 12/445,570 Office Action dated May 22, 2012.
U.S. Appl. No. 12/788,190 Office Action dated Jul. 16, 2012.
U.S. Appl. No. 13/284,741 Office Action dated May 17, 2012.
U.S. Appl. No. 13/007,518 Office Action dated Sep. 12, 2012.
Dobak, Formulations and Methods for Activating Brown Adipose Tissue,' U.S. Appl. No. 12/760,258, filed Apr. 14, 2010, Unpublished.
Dobak, "Formulations for Treatment of Adipose Tissue, Cutaneous Tissue and Disorders, and Muscular Tissue." U.S. Appl. No. 12/445,571, filed Jan. 22, 2010, Unpublished.
Dobak, "Methods, Compositions, and Formulations for the Treatment of Thyroid Eye Disease." U.S. Appl. No. 12/445,570, filed Jan. 12, 2010, Unpublished.
Shishiba, "Selection of Treatment Methods for Basedow's disease," Modern Physician 23, ED. 7, pp. 1103-1111 (2003).
Adcock, "Molecular interactions between glucocorticoids and long-acting $β_2$-agonists," J Allergy Clin Immunol 110(6 Suppl):S261-8 (2002).
Arner et al., "Human fat cell lipolysis: biochemistry, regulation and clinical role," Best Practice & Research Clinical Endocrinology & Metabolism 19:471-482 (2005).
Arner, et al. "Adrenergic Regulation of Lipolysis in Situ at Rest and during Exercise," J. Clin, Invest., vol. 85, pp. 893-898 (1990).
Arner, et al., "In Vivo Interactions between Beta-1 and Beta-2 Adrenoceptors Regulate Catecholamine Tachyphylaxia in Human Adipose Tissue," Journ. Pharm. Exper. Therap., vol. 259, No. 1, pp. 317-322 (1991).
Arner, et al., "Adrenergic Receptor Function in Fat Cells1-3," Am. J. Clin. Nutr. 55:228S-36S (1992).
Barbe, et al., "In situ assessment of the role of the β1-, β2- and β3 adrenoceptors in the control of lipolysis and nutritive blood flow in human subcutaneous adipose tissue," British Journ. Pharma. (1996) 11 (7 pgs.).
Barbe, et al., "In Vivo Increase in β-Adrenergic Lipolytic Response in Subcutaneous Adipose Tissue of Obese Subject Submitted to a Hypocaloric Diet," Journ. Clin. Endocrin. And Metab., vol. 82, No. 1, pp. 63-69 (1997).
Barnes, "Scientific rationale for inhaled combination therapy with long-acting β2-agonists and corticosteroids," Eur Respir Journ. 19:182-191 (2002).
Bartalena et al., "Management of Graves' Ophthalmopathy: Reality and Perspectives," Endocrine Reviews 21(2): 168-199 (2000).
Bartley, "The Epidemiologic Characteristics and Clinical Course of Ophthalmopathy Associated with Autoimmune Thyroid Disease in Olmstead County, Minnesota," Th. Am. Ophth. Soc., vol. XCII, (112 pgs.)(1994).
Bartley et al, "Clinical Features of Graves' Ophthalmopathy in an Incidence Cohort," Amer. Journ. Ophthalmology, 121:284-290 (1996).
Basadonna et al., "Plantar Fat Pad Atrophy After Corticosteroid Injection for an Interdigital Neuroma," Amer. Journ. Phys. Med. Rehabil. 1999; 78:283-285.
Beers, et al. "The Merck Manual" 706-707 (1999).
Benovic et al.. "Regulation of adenylyl cyclase-coupled β-adrenergic receptors." Ann Rev Cell Biol 1988;4: 405-428.
Benzon et al., "Comparison of the Particle Sizes of Different Steroids and the Effect of Dilution," Anesthesiology, 106:33 1-8 (2007).
Bordaberry et al., "Repeated Peribulbar Injections of Triamcinolone Acetonide: a Successful and Safe Treatment for Moderate to Severe Graves' Opthalmopathy," ACTA Ophthalmologica 2009: 87:58-64.

(56) References Cited

OTHER PUBLICATIONS

Bousquet-Melou, "beta-Adrenergic control of lipolysis in primate white fat cells: a comparative study with nonprimate mammals," Am J Physiol Regulatory Integrative Comp Physiol 267:115-123 (1994).
Brodde et al., "Terbutaline-induced desensitization of human lymphocyte beta 2-adrenoceptors. Accelerated restoration of beta-adrenoceptor responsiveness by prednisone and ketotifen," J Clin Invest 76(3):1096-101 (1985).
Bronnegard et al., "Effect of glucocorticosteroid treatment on glucocorticoid receptor expression in human adipocytes," J Clin Endocrinol Metab 80(12):3608-12 (1995).
Burns, et al. "Regulation of lipolysis . . . " Lancet 1 (7441): 797-798 (1966).
Bujalska et al., "Characterisation of 11β-hydroxysteroid dehydrogenase 1 in human orbital adipose tissue: a comparison with subcutaneous and omental fat," J Endocrinol 192(2):279-88 (2007).
Carpene et al., "Adrenergic lipolysis in guinea pig is not a beta 3-adrenergic response: comparison with human adipocytes," Am J Physiol Regulatory Integrative Comp Physiol 266:905-913 (1994).
Caruso et al., "Topical fat reduction from the waist," Diabetes Obesity Metabolism 9:300-303 (2007).
Caruso et al. "An evaluation of mesotherapy solutions for inducing . . . " J Plast Reconstr Aesthet Surg. 61(11):1321-4, Epub2007 (2008).
Chung, "The complementary role of glucocorticosteroids and long-acting beta-adrenergic agonists," Allergy 53(42 Suppl):7-13 (1998).
Clauser et al., "Rationale of Treatment in Graves Ophlhalmopathy," Plastic and Reconstructive Surgery, vol. 108, pp. 1880-1894 Dec. (2001).
Collins et al., "Learning new tricks from old dogs: β-adrenergic receptors teach new lessons on firing up adipose tissue metabolism," Molecular Endocrinology First published Jul. 8, 2004 as doi:10.1210/me.2004-0193 (22 pgs.) (2004).
Cuirong, Study on the Effect of Hyaluronidase on Orbital Fibroblast, Chinese M.M. thesis, 2006, p. 2.
De Mazancourt et al., "Correction by dexamethasone treatment of the altered lipolytic cascade induced by adrenalectomy in rat adipocytes," Horm Metab Res 22(1):22-4 (1990).
De Ponte et al., "New Approach to the Surgical Treatment of Severe Exophthalmos in Graves Disease," J. Craniofacial Surgery, vol. 9, No. 4, pp. 394-399 (1998).
Farias-Silva et al., "Glucocorticoid receptor and Beta-adrenoceptor expression in epididymal adipose tissue from stressed rats," Ann N Y Acad Sci 1018:328-32 (2004).
Farias-Silva et al., "Stress-induces alteration in the lipolytic response to β-adrenoceptor agonists in rat white adipocytes," Journal of Lipid Research, vol. 40, 1719-1727 (1999).
Flechtner-Mors et al., "In Vivo α1-Adrenergic Lipolytic Activity in Subcutaneous Adipose Tissue of Obese Subjects," Journ. of Pharm. and Exper. Therap., vol. 301, No. 1, pp. 229-233 (2002).
Fries, "Thyroid dysfunction: managing the ocular complications of Graves' disease," Geriatrics 47(2):58-60, 63-4, 70 (1992).
Fuller et al., "Fluticasone propionate—an update on preclinical and clinical experience," Respir Med 89 Suppl A:3-18 (1995).
Galitzky et al., "Coexistence of β1-, β2-, and β3-adrenoceptors in dog fat cells and their differential activation by catecholamines," The Amer. Physiol. Society pp. E403-E412 (1993).
Galitzky et al., "Differential activation of β1-, β2-, and β3-adrenoceptors by catecholamines in white and brown adipocytes," Fundam. Clin. Pharmacol 9, 324-331 (1995).
Germack et al., "β-Adrenoceptor subtype expression and function in rat white adipocytes," British Journ. Pharma. 120, 201-210 (1997).
Gettys et al., "Age-Dependent Changes in β-Adrenergic Receptor Subtypes and Adenylyl Cyclase Activation in Adipocytes from Fischer 344 Rats," Endocrinology, vol. 136, No. 5, pp. 2022-2032 (1995).
Gibaud et al., "Poly(ε-caprolactone) and Eudragit microparticles containing fludrocortisone acetate," Int J Pharm 28;269(2):491-508 (2004).
Gittoes and Franklyn, "Hyperthyroidism. Current treatment guidelines," Drugs 55(4):543-53 (1998).
Giudicelli et al., Eur J Biochem 99(3):457-62 (1979).
Goodman "Permissive effects of hormones . . . " Endocrinology 86 (5):1064-1074 (1970).
Greenway et al., "Topical Fat Reduction," Obesity Research, vol. 3 Suppl. 561S-568S (1995).
Gronnenberg "Effects of Local . . . " Allergy 51(10):685-692 (1996).
Hadcock and Malbon, "Regulation of β-adrenergic receptors by "permissive" hormones: glucocorticoids increase steady-state levels of receptor mRNA," Proc Natl Acad Sci U S A 85(22):8415-9 (1988).
Hall, et al. "Intravenous methylpredinisolone in the treatment of Graves; ophthalmopathy" BMJ 297(6663) 1574-1578 (1988).
Heine et al., "Increased adipose tissue in male and female estrogen receptor-α knockout mice,"PNAS, vol. 97, No. 23 12729-72734 (2000).
Hickey et al., Biomaterials 23:1649-1656, 2002.
Hiromatsu Basedow's disease Japanese Publication New Regional Sales, No. 1, Syndromes, (2006).
January et al., "Salmeterol-induced desensitization, internalization and phosphorylation of the human β2-adrenoceptor," British Journal of Pharmacology 123:701-711 (1998).
Jockers et al,, "Desensitization of the β-Adrenergic Response in Human Brown Adipocytes," Endocrinology, vol. 139, No. 6, pp. 2676-2684 (1998).
Johnson, "The β-Adrenoceptor," Am J Resp Crit Care Med 158:146-153 (1998).
Johnson, "β-2-adrenoceptors: mechanisms of action of β-2-agonists," Ped Resp Rev 2:57-62 (2001).
Johnson, "Interactions between Corticosteroids and β2-Agonists in Asthma and Chronic Obstructive Pulmonary Disease," Proc Am Thorac Soc, vol. 1, pp. 200-206 (2004).
Johnson et al. "The pharmacology of salmeterol." Life Sci 1993; 52: 2131-2143.
Kazim et al., "Reversal of dysthyroid optic neuropathy following orbital fat decompression," Br. J. Ophthalmol. 84:600-605 (2000).
Kendall-Taylor et al., "Intravenous methylprednisolone in the treatment of Graves' ophthalmopathy," BMJ 297(6663):1574-8 (1988).
Kolata "Calorie-burning fat? Studies say you have it" The New York Times, (Apr. 8, 2009).
Kumar et al., "Evidence for Enhanced Adipogenesis in the Orbits of Patients with Graves' Ophthalmopathy," Journ. Clin. Endocrin. & Metab. 89(2):930-935 (2004).
Lacasa et al., "Permissive action of glucocorticoids on catecholamine-induced lipolysis: direct "in vitro" effects on the fat cell beta-adrenoreceptor-coupled-adenylate cyclase system," Biochem Biophys Res Commun 153(2):489-97 (1988).
Lafontan. "Fat Cells: Afferent and efferent messages define new approaches to treat obesity." Ann Rev Pharmacol. Toxicol 45; 119-146, (2005).
Lafontan and Berlan "Fat cell adrenergic receptors and the control of white and brown fat cell function" J Lipid Res 34:1057-1091 (1993).
Lai et al., "Dexamethasome Regulates the β-Adrenergic Receptor Subtype Expressed by 3T3-L1 Preadipocytes and Adipocytes," Journ. Biol. Chem. vol. 257, No. 12, pp. 6691-6696 (1982).
Langley et al., "Perioperative management of the thyrotoxic patient," Endocrinol Metab Clin North Am 32(2):519-34 (2003).
Laurent and Scopes "Hyaluronidase in the treatment . . . " Lancet 269 Edition No. 6889 pp. 537-538 (1955).
Lonnqvist et al., "Lipolytic Catecholamine Resistance Due to Decreased β2-Adrenoceptor Expression in Fat Cells," J. Clin. Invest, vol. 90, pp. 2175-2186 (1992).
Louis, et al. "Role of β-Adrenergic Receptor . . . " Cardiovascular Drugs and Therapy 14(6):565-577(2000).
Mak et al., "Protective effects of a glucocorticoid on downregulation of pulmonary beta 2-adrenergic receptors in vivo," J Clin Invest 96(1):99-106 (1995).
Marcocci et al., "Orbital cobalt irradiation combined with retrobulbar or systemic corticosteroids for Graves' ophthalmopathy: a compartitive study," Clin Endocrinol (Oxf) 27(1):33-42 (1987).

(56) References Cited

OTHER PUBLICATIONS

Mattson "Does brown fat protect against diseases of aging?" Ageing Res Rev 9(1):69-76 (2010).
Mauriege et al., "Human fat cell beta-adrenergic receptors: beta-agonist-dependent lipolytic responses and characterization of beta-adrenergic binding sites on human fat cell membranes with highly selective beta1-antagonists," Journ. Lipid Research, vol. 29, pp. 587-601 (1988).
Mersmann "Beta-Adrenergic receptor modulation . . . " J. Animal Science 80:E24-E29 (2002).
Mirkin, "Albuterol for weight control," www.DrMirkin.com (2009).
Mori et al.. "Rapid desensitization of lipolysis in the visceral and subcutaneous adipocytes of rats." Lipids 2007; 42(4): 307-314.
Murano, "Selection of Treatment Methods for Basedow's disease" Modern Physician 23 Ed 7, pp. 1103-1111 (2003).
Nakai, et al. "Hypothyroid Grave's Disease concurring with . . . " Industrial Medical University Magazine 25(3):333-339 (2003).
Ng et al., "Combined orbital irradiation and systemic steroids compared with systemic steroids alone in the management of moderate-to-severe Graves' ophthalmopathy: a preliminary study," Hong Kong Med. J., vol. 11, No. 5, pp. 322-330 (2005).
Ohkawara et al., "Glucorticoid-Induced Alteration of Beta-Adrenergic Adenylate Cyclase Response of Epidermis," Arch Dermatol Res 277:88-92 (1985).
Ohtsuka et al., "Effect of Steroid Pulse Therapy With and Without Orbital Radiotherapy on Graves' Ophthalmopathy," Am J Ophthalmol 135:285-290 (2003).
Page et al., "β-Adrenergic receptor agonists increase apoptosis of adipose tissue in mice," Domest Anim Endoerinol 26(1):23-31 (2004).
Papadopoulos et al., "The Clinical Picture: Soft Tissue Atrophy After Corticosteroid Injection," Cleveland Clinic Journ. Med., 2009; vol. 76 (6)373-374.
Pedersen et al., "Anti-glucoeorticaid effects of progesterone in vivo on rat adipose tissue metabolism," Steroids 68:543-550 (2003).
Reynisdottir et al., "Effect of glucocorticosteroid treatment on beta-adrenoceptor subtype function in adipocytes from patients with asthma," Clin Sci 85(2):237-44 (1993).
Risse-Sundermann, "The treatment of alopecia areata by intradermal injections of microcrystallized prednisone trimethylacetate," Dtsch med Wochertschr 85(15):584-586 (1960).
Seco et al., "Acute and chronic treatment with glucocorticosteroids, modifying the beta 2-adrenergic response of the guinea pig trachea," Lung 173(5):321-8 (1995).
Sharma et al., "β-Adrenergic Receptor Blockers and Weight Gain A Systemic Analysis," Hypertension 37:250-254 (2001).
Taouis et al., "Characterization of Dog Fat Cell Adrenoceptors: Variations in Alpha-2 and Beta Adrenergic Receptors Distribution According to the Extent of the Fat Deposits and the Anatomical location," Journ. Karma. and Exper. Therap., vol. 242, No. 3, pp. 1041-1049 (1987).
West, "Solid state chemistry and its applications," Wiley, New York pp. 358-365 (1988).
Wiersinga and Prummel, "Graves' ophthalimpathy: a rational approach to treatment," Trends Endocrinol Metab 13(7):280-7 (2002).
Yip. et al. "Growth hormones and dexamethasone . . . " Endicrinology 140(3):1219-1227 (1999).
Yokoyama "Basedow's Disease Diagnosis and Treatment" 93rd edition No. 7 pp. 1077-1081 (2005).
Office action mailed Jan. 6, 2010 in connection with U.S. Appl. No. 11/457,436.
Office action mailed Aug. 24, 2009 in connection with U.S. Appl. No. 11/457,436.
GB 0718905.3 combined search and examination report dated Jan. 28, 2008.
GB 0718905.3 search report dated Nov. 27, 2008, claims 31-33.
GB 0718905.3 search report dated Nov. 27, 2008, claims 34-37 and 44.
GB 0718905.3 examination report dated Nov. 27, 2008.
AU2006270165 examiner's first report dated Dec. 24, 2009.
GB 0804401.8 search report dated Apr. 15, 2009.
PCT/US2007/079740 search report mailed Jan. 30, 2008.
EP 07871172 supplementary European search report dated Mar. 1, 2010.
PCT/US2007/081568 search report mailed Jun. 17, 2008.
PCT/US10/36484 Search Rpt & Written Opn. Mailed Feb. 21, 2011.
PCT/US10/36484 IPRP mailed Nov. 29, 2011 w Written Opinion.
EP07843370 Search Rpt mailed Mar. 11, 2010.
EP07843370 Ext. Srch. Rpt. Mailed Feb. 26, 2010.
EP06787329.9 Office Action mailed Jan. 31, 2011.
EP06787329.9 Extended European search rpt dated Mar. 12, 2010.
EP 11180982 Search Report mailed Nov. 21, 2011.
GB 1008885.4 Combined search and examination rpt dated Sep. 29, 2010.
GB 1100628.5 Search and Examination Report mailed Apr. 11, 2011.
GB 1120091.2 Search and Examination Report mailed Dec. 9, 2011.
GB 1120090.4 Search and Examination Report mailed Dec. 9, 2011.
PCT/US2011/021424 International Search Report mailed Sep. 21, 2011.
IL 198184 Exam Report mailed Dec. 4, 2011.
GB 1100628.5 Examination Report mailed Feb. 6, 2012.
GB 1008885.4 Examination Report mailed Nov. 18, 2011.
Dobak, "Formulations for Treatment of Adipose Tissue, Cutaneous Tissue and Disorders, and Muscular Tissue," U.S. Appl. No. 12/445,571, filed Jan. 22, 2010.
Dobak, "Methods, Compositions, and Formulations for the Treatment of Thyroid Eye Disease," U.S. Appl. No. 12/445,570, filed Jan. 12, 2010.
U.S. Appl. No. 12/760,258, filed Apr. 14, 2010, Unpublished.
U.S. Appl. No. 13/204,423, filed Aug. 5, 2011, Unpublished.
U.S. Appl. No. 13/284,741, filed Oct. 28, 2011, Unpublished.
U.S. Appl. No. 13/303,046, filed Nov. 22, 2011, Unpublished.
AU2011205646 Examination Report dated Jul. 3, 2014.
CA2,761,744 Examination Report dated Jul. 15, 2014.
Cazzola et al. Novel long-acting bronchodilators for COPD and asthma. BR J Pharmacol. 155(3):291-299 (2008).
CN200680031397.4 Office Action dated Aug. 5, 2014 (w/English translation).
CN200680031397.4 Office Action dated May 23, 2013 (w/English translation).
CN201080023277.6 Office Action dated Jul. 7, 2014 (w/English translation).
CN201180013558.8 Office Action dated Apr. 21, 2014 (w/English translation).
CN201180056619.9 Office Action dated Jul. 3, 2014 (w/English translation).
EP11844295.3 Extended Search Report dated Nov. 6, 2014.
EP10781245.5 Extended Search Report dated Jan. 27, 2014.
EP11733493.8 Extended Search Report dated Feb. 27, 2014.
GB0718905.3 Examination Report dated Feb. 10, 2014.
GB1207749.1 Office Action dated May 13, 2014.
GB1207749 Office Action dated Sep. 19, 2014.
GB1207749.1 Office Action dated Oct. 24, 2014.
GB1120090.4 Office Action dated Oct. 9, 2014.
Greenway et al. Regional Fat Loss from the Thigh in Obese Women after Adrenergic Modulation. Clin. Ther. 9(6): 663-9 (1987).
IL198184 Office Action dated Jan. 23, 2014 (w/English translation).
IL198184 Office Action dated Jun. 30, 2014 (w/English Translation).
JP2009-533423 Office Action dated Aug. 2, 2011 (w/English translation).
JP2009-533423 Office Action dated Jun. 3, 2014 (w/English Translation).
JP2011083171 Office Action dated May 20, 2014 (w/English translation).
JP2012-095792 Office Action dated Sep. 24, 2014 (w/English Translation).
JP2009-533423 Appeal No. 2012-7183 Trial Decision dated Oct. 28, 2014 (w/English translation).
KR-10-2009-7009972 Office Action dated Dec. 6, 2010 (w/English Translation).

(56) References Cited

OTHER PUBLICATIONS

KR-10-2011-7031166 Notice of Allowance dated May 30, 2014 (w/English Translation).
KR-10-2012-7021302 Office action dated Aug. 21, 2014 (w/English Translation).
MX/a/2008/000570 Office Action dated Jan. 21, 2013 (w/English Translation).
MX/a/2008/000570 Office Action dated Nov. 18, 2011 (w/English Translation).
MX/a/2008/000570 Office Action dated Apr. 7, 2011 (w/English Translation).
MX/a/2009/004198 Office Action dated Jan. 5, 2013 (w/English Translation).
MX/a/2009/004199 Office Action dated Apr. 16, 2012 (w/English Translation).
MX/a/2011/012542 Office Action dated Apr. 10, 2013 (w/English Translation).
MX/a/2011/012542 Office Action dated Jul. 15, 2013 (w/English Translation).
MX/a/2011/012542 Office Action dated Jun. 12, 2014 (w/English translation).
NCBI PubChem Compound Summary for Isoproterenol. https://pubchem.ncbi.nim.nih.gov/summary/summary.cgi?cid=3779 &loc=ex_rcs. Sep. 7, 2014.
NCBI PubChem Compound Summary for Dobutamine/https://pubchem.ncbi.nim.nih.gov/summary/summary.cgi?cid=36811 &loc=rcs. Sep. 4, 2014.
NCBI PubChem Compound Summary for Salbutamol. https://pubchem.ncbi.nlm.nih.gov/summary/summary.cgi?sid=564130578,viewopt=Pub Chem. Sep. 16, 2014.
NCBI PubChem Compound Summary for Fluticasone Propionate. https://pubchem.ncbi.nlm.nih.gov/summary/summary.cgi?sid=444036. Sep. 11, 2014.
Schiffelers et al. Lipolytic and nutritive blood flow response to beta-adrenoceptor stimulation in situ in subcutaneous abdominal adipose tissue in obese men. International Journal of Obesity. 27:227-231 (2003).
SG201304014-2 Written Opinion and Search Report dated Jun. 17, 2014 (English Translation only).
Tulloch-Reid et al. Do Measures of Body Fat Distribution Provide Information on the Risk of Type 2 Diabetes in Addition to Measures of General Obesity. Diabetes Care. 26(9): 255661 (Sep. 2003).
U.S. Appl. No. 12/788,190 Office Action dated Aug. 14, 2014.
U.S. Appl. No. 12/788,190 Office Action dated Mar. 26, 2014.
U.S. Appl. No. 13/204,423 Office Action dated Apr. 10, 2014.
U.S. Appl. No. 13/007,518 Office Action dated Nov. 4, 2014.
U.S. Appl. No. 13/284,741 Response to Non-Final Rejection filed Aug. 17, 2012.
U.S. Appl. No. 13/284,741 Restriction Requirement dated Feb. 17, 2012.
U.S. Appl. No. 13/284,741 Response to Restriction Requirement dated Mar. 13, 2012.
U.S. Appl. No. 13/284,741 Notice of Allowance mailed Jan. 2, 2013.
U.S. Appl. No. 11/457,436 Response to Non-final Rejection dated Oct. 21, 2009.
U.S. Appl. No. 90/013,336 Ex Parte Reexamination Communication and Order Granting Ex Parte Reexamination dated Oct. 7, 2014.
U.S. Appl. No. 90/013,336 Ex Parte Reexamination filed Sep. 3, 2014.
U.S. Appl. No. 90/013,336 Ex Parte Reexamination filed Sep. 3, 2014, Exhibit A: U.S. Pat. No. 8,420,625.
U.S. Appl. No. 90/013,336 Ex Parte Reexamination filed Sep. 3, 2014, Exhibit B: U.S. Pat. No. 4,525,359, filed by Greenway on Dec. 10, 1982, and issued Jun. 25, 1985.
U.S. Appl. No. 90/013,336 Ex Parte Reexamination filed Sep. 3, 2014, Exhibit C: U.S. Patent Publication No. 2004/0235922, filed by Baile et al. on May 14, 2004, and published on Nov. 25, 2004.
U.S. Appl. No. 90/013,336 Ex Parte Reexamination filed Sep. 3, 2014, Exhibit D: U.S. Patent Publication No. 2005/0113456 filed by Aberg on Nov. 12, 2004, and published on May 26, 2005.
U.S. Appl. No. 90/013,336 Ex Parte Reexamination filed Sep. 3, 2014, Exhibit E: Publication by Linden et al. dated 1996.
U.S. Appl. No. 90/013,336 Ex Parte Reexamination filed Sep. 3, 2014, Exhibit F: U.S. Appl. No. 12/763,030, filed on Apr. 19, 2010, now Pub. No. 2011/0105446.
U.S. Appl. No. 90/013,336 Ex Parte Reexamination filed Sep. 3, 2014, Exhibit G: U.S. Appl. No. 11/457,436, filed Jul. 13, 2006, now U.S. Pat. No. 7,829,554.
U.S. Appl. No. 90/013,336 Ex Parte Reexamination filed Sep. 3, 2014, Exhibit H: U.S. Appl. No. 60/732,981, filed Nov. 3, 2005.
U.S. Appl. No. 90/013,336 Ex Parte Reexamination filed Sep. 3, 2014, Exhibit I: U.S. Appl. No. 60/729,531, filed Oct. 24, 2008.
U.S. Appl. No. 90/013,336 Ex Parte Reexamination filed Sep. 3, 2014, Exhibit J: U.S. Appl. No. 60/699,155, filed Jul. 14, 2005.
U.S. Appl. No. 90/013,336 Ex Parte Reexamination filed Sep. 3, 2014, Exhibit K: U.S. Appl. No. 13/096,895 Office Action dated Jun. 26, 2012.
U.S. Appl. No. 90/013,336 Ex Parte Reexamination filed Sep. 3, 2014, Exhibit L: U.S. Appl. No. 13/096,895 Response to Non-Final Office Action dated Dec. 20, 2012.
U.S. Appl. No. 90/013,336 Ex Parte Reexamination filed Sep. 3, 2014, Exhibit M: U.S. Appl. No. 13/096,895 Applicant Initiated Interview Summary dated Jan. 29, 2013.
U.S. Appl. No. 90/013,336 Ex Parte Reexamination filed Sep. 3, 2014, Exhibit N: U.S. Appl. No. 13/096,895 Examiner Initiated Interview Summary dated Feb. 11, 2013.
U.S. Appl. No. 90/013,336 Ex Parte Reexamination filed Sep. 3, 2014, Exhibit O: U.S. Appl. No. 13/096,895 Supplemental Amendment and Response to Interview Summary dated Feb. 8, 2013.
U.S. Appl. No. 90/013,336 Ex Parte Reexamination filed Sep. 3, 2014, Exhibit P: U.S. Appl. No. 13/096,895 Notice of Allowance and Allowability dated Feb. 27, 2013.
U.S. Appl. No. 90/013,336 Ex Parte Reexamination filed Sep. 3, 2014, Exhibit Q: U.S. Appl. No. 12/763,030 Response to Final Office Action dated Jun. 12, 2013.
U.S. Appl. No. 90/013,336 Ex Parte Reexamination filed Sep. 3, 2014, Exhibit R: U.S. Appl. No. 13/096,895 Terminal Disclaimer for U.S. Appl. No. 12/763,030, filed Feb. 7, 2013.
U.S. Appl. No. 90/013,336 Ex Parte Reexamination filed Sep. 3, 2014, Exhibit S: U.S. Appl. No. 12/763,030 Examiner Initiated Interview Summary dated Nov. 13, 2013.
U.S. Appl. No. 90/013,336 Ex Parte Reexamination filed Sep. 3, 2014, Exhibit T: NCBI PubChem Compound Summary for Isoproterenol.
U.S. Appl. No. 90/013,336 Ex Parte Reexamination filed Sep. 3, 2014, Exhibit U, Tulloch-Reid et al. Do Measures of body Fat Distribution Provide Information on the Risk of Type 2 Diabetes in Addition to Measures of General Obesity. Diabetes Care. 26:2556-2561. 2003.
U.S. Appl. No. 90/013,336 Ex Parte Reexamination filed Sep. 3, 2014, Exhibit V: U.S. Appl. No. 60/470,924.
U.S. Appl. No. 90/013,336 Ex Parte Reexamination filed Sep. 3, 2014, Exhibit W: U.S. Appl. No. 60/524,376.
U.S. Appl. No. 90/013,348 Ex Parte Reexamination filed Sep. 19, 2014.
U.S. Appl. No. 90/013,348 Ex Parte Reexamination filed Sep. 19, 2014, Appendix 1.
U.S. Appl. No. 90/013,348 Ex Parte Reexamination filed Sep. 19, 2014, Appendix 2.
U.S. Appl. No. 90/013,348 Ex Parte Reexamination filed Sep. 19, 2014, Appendix 3.
U.S. Appl. No. 90/013,348 Ex Parte Reexamination filed Sep. 19, 2014, Appendix 4.
U.S. Appl. No. 90/013,348 Ex Parte Reexamination filed Sep. 19, 2014, Appendix 5.
U.S. Appl. No. 90/013,348 Ex Parte Reexamination filed Sep. 19, 2014, Exhibit A: U.S. Pat. No. 8,404,750.
U.S. Appl. No. 90/013,348 Ex Parte Reexamination filed Sep. 19, 2014, Exhibit B: European Patent Publication No. EP 0120165.

(56) References Cited

OTHER PUBLICATIONS

U.S. Appl. No. 90/013,348 Ex Parte Reexamination filed Sep. 19, 2014, Exhibit C. U.S. Patent Publication No. 2004/0235922.
U.S. Appl. No. 90/013,348 Ex Parte Reexamination filed Sep. 19, 2014, Exhibit D. U.S. Patent Publication No. 2005/0113456.
U.S. Appl. No. 90/013,348 Ex Parte Reexamination filed Sep. 19, 2014, Exhibit E: Publication by Linden et al. Pharmacological Basis for Duration of Effect: Formoterol and Salmeterol Versus Short-Acting 132-Adrenoceptor Agonists. Lung 174:1-22 (1996).
U.S. Appl. No. 90/013,348 Ex Parte Reexamination filed Sep. 19, 2014, Exhibit F: Publication by Schiffelers et al. Lipolytic and nutritive blood flow response to P-adrenoceptor stimulation in situ in subcutaneous abdominal adipose tissue in obese men. International J. of Obesity 27: 227-231 (2003).
U.S. Appl. No. 90/013,348 Ex Parte Reexamination filed Sep. 19, 2014, Exhibit G: U.S. Patent Publication No. 2007/0014843 A1.
U.S. Appl. No. 90/013,348 Ex Parte Reexamination filed Sep. 19, 2014, Exhibit H: U.S. Appl. No. 13/284,741, filed Jul. 13, 2006.
U.S. Appl. No. 90/013,348 Ex Parte Reexamination filed Sep. 19, 2014, Exhibit I: U.S. Appl. No. 12/788,190, filed May 26, 2010.
U.S. Appl. No. 90/013,348 Ex Parte Reexamination filed Sep. 19, 2014, Exhibit J: U.S. Appl. No. 61/181,627.
U.S. Appl. No. 90/013,348 Ex Parte Reexamination filed Sep. 19, 2014, Exhibit K: U.S. Appl. No. 61/251,624.
U.S. Appl. No. 90/013,348 Ex Parte Reexamination filed Sep. 19, 2014, Exhibit L: U.S. Appl. No. 61/289,972.
U.S. Appl. No. 90/013,348 Ex Parte Reexamination filed Sep. 19, 2014, Exhibit M: U.S. Appl. No. 13/284,741 Non-final Rejection mailed May 17, 2012.
U.S. Appl. No. 90/013,348 Ex Parte Reexamination filed Sep. 19, 2014, Exhibit N: U.S. Appl. No. 13/284,741 Response to Non-final Rejection dated Aug. 17, 2012.
U.S. Appl. No. 90/013,348 Ex Parte Reexamination filed Sep. 19, 2014, Exhibit 0: U.S. Appl. No. 13/284,741 Restriction Requirement mailed Feb. 17, 2012.
U.S. Appl. No. 90/013,348 Ex Parte Reexamination filed Sep. 19, 2014, Exhibit P: U.S. Appl. No. 13/284,741 Response to Restriction Requirement dated Mar. 13, 2012.
U.S. Appl. No. 90/013,348 Ex Parte Reexamination filed Sep. 19, 2014, Exhibit Q: U.S. Appl. No. 13/284,741 Notice of Allowance mailed Jan. 2, 2013.
U.S. Appl. No. 90/013,348 Ex Parte Reexamination filed Sep. 19, 2014, Exhibit R: U.S. Appl. No. 11/457,436.
U.S. Appl. No. 90/013,348 Ex Parte Reexamination filed Sep. 19, 2014, Exhibit S: U.S. Pat. No. 7,829,554.
U.S. Appl. No. 90/013,348 Ex Parte Reexamination filed Sep. 19, 2014, Exhibit T. U.S. Appl. No. 11/457,436 Non-final Rejection mailed Aug. 24, 2009.
U.S. Appl. No. 90/013,348 Ex Parte Reexamination filed Sep. 19, 2014, Exhibit U: Response to Non-final Rejection dated Oct. 21, 2009.
U.S. Appl. No. 90/013,348 Ex Parte Reexamination filed Sep. 19, 2014, Exhibit V: NCBI PubChem Compound Summary for Isoproterenol.
U.S. Appl. No. 90/013,348 Ex Parte Reexamination filed Sep. 19, 2014, Exhibit W: Publication by Frank L. Greenway and George A Bray. Regional Fat Loss from the Thigh in Obese Women after Adrenergic Modulation. Clin. Ther. 9(6): 663-9 (1987).
U.S. Appl. No. 90/013,348 Ex Parte Reexamination filed Sep. 19, 2014, Exhibit X. Publication by Marshall K. Tulloch-Reid et al. Do Measures of Body Fat Distribution Provide Information on the Risk of Type 2 Diabetes in Addition to Measures of General Obesity. Diabetes Care. 26(9): 255661 (Sep. 2003).
U.S. Appl. No. 90/013,348 Ex Parte Reexamination filed Sep. 19, 2014, Exhibit Y: NCBI PubChem Compound Summary for Dobutamine.
U.S. Appl. No. 90/013,348 Ex Parte Reexamination filed Sep. 19, 2014, Exhibit Z: NCBI PubChem Compound Summary for Salbutamol.
U.S. Appl. No. 90/013,348 Ex Parte Reexamination filed Sep. 19, 2014, Exhibit AA: NCBI PubChem Compound Summary for Fluticasone Propionate.
Wang et al, Preparation of Hydrophobic Drugs Cyclodextrin Complex by Lyophilization Monophase Solution, Drug Development and Industrial Pharmacy, 32:73-83 (2006).
Boulet et al., "Influence of obesity on response to fluticasone with or without salmeterol in moderate asthma," Respiratory Medicine (2007) 101, 2240-2247.
CN 200680031397.4 Office Action dated Feb. 14, 2012.
CN 200780046741.1 Office Action dates Feb. 22, 2012.
EP 11180982.8 Exam Report dated Mar. 14, 2012.
GB 1008885.4 Exam Report dated Apr. 4, 2012.
GB 1100628.5 Exam Report dated Feb. 6, 2012.
IL 198183 translation of Office Action dated Dec. 4, 2011.
U.S. Appl. No. 13/204,423 Office Action dated May 1, 2012.
U.S. Appl. No. 12/760,258 Office Action dated Apr. 2, 2012.
U.S. Appl. No. 12/763,030 Office Action dated May 7, 2012.
AU2011205646 Examination Report dated Jan. 7, 2013.
CA 2,761,744 Examination Report dated Dec. 28, 2012.
CA 2,786,618 Examination Report dated May 21, 2013.
CN 200680031397.4 Office Action dated Jan. 25, 2013 (English translation only).
CN 200780046741.1 Office Action dated Nov. 20, 2012 (English translation only).
CN 201080023277.6 Office Action dated Dec. 26, 2012 (English translation only).
CN200780046741.1 Office Action dated Aug. 8, 2013 (English translation only).
CN201180013558.8 Office Action dated May 28, 2013 (English translation only).
EA 201270683/26 Office Action dated Dec. 5, 2012 (English translation only).
Finney et al., Chronic systemic administration of salmeterol to rats promotes pulmonary beta(2)-adrenoceptor desensitization and down-regulation of G(s alpha), Br. J. Pharmacol., vol. 132, No. 6, pp. 1261-1270 (2001).
GB1008885.4 Examination Report dated Jan. 8, 2013.
Hoffman, R. J., et al., "Clenbuterol ingestion causing prolonged tachycardia, hypokalemia, and hypophosphatemia with confirmation by quantitative levels," J. of Toxicology, Clinical Toxicology, 2001, 39(4), 339-344.
IL 198184 Office Action dated Jan. 20, 2013 (English translation only).
JP 2011083171 Office Action dated Mar. 21, 2013 (English translation only).
Kim et al., "Prevention and reversal of pulmonary inflammation and airway hyperresponsiveness by dexamethasone treatment in a murine model of asthma induced by house dust," Am. J. Physiol Lung Cell Mol Physiol., vol. 287, No. 3, pp. L503-L509 (2004).
KR-10-2011-7031166 Office Action dated Jul. 17, 2013 (English translation only).
MX/A/2009/004198 Exam Report dated May 29, 2012 (English translation only).
PCT/US07/079740 Search rpt mailed Jan. 30, 2008.
PCT/US07/081568 Search rpt mailed Jun. 17, 2008.
PCT/US2011/061972 International Preliminary Report on Patentability and Written Opinion dated May 28, 2013.
PCT/US2011/061973 International Preliminary Report on Patentability and Written Opinion dated May 28, 2013.
Ryall et al., "Intramuscular beta2-agonist administration enhances early regeneration and functional repair in rat skeletal muscle after myotoxic injury," Journal of Applied Physiology, 2008, vol. 105, pp. 165-172.
Schwegman et al., "Practical Formulation and Process Development of Freeze-Dried Products," Pharmaceutical Development and Technology 10:151-173 (2005).
SG 201108652-7 Search Report dated Mar. 4, 2013 (English translation only).
Teagarden et al., "Practical aspects of lyophilization using non-aqueous co-solvent systems," Eur J. Pharm Sci., 15(2):115-33 (2002).
U.S. Appl. No. 12/445,570 Office Action dated Mar. 6, 2013.

(56) References Cited

OTHER PUBLICATIONS

U.S. Appl. No. 12/763,030 Office Action dated Dec. 12, 2012.
U.S. Appl. No. 12/788,190 Office Action dated May 8, 2013.
U.S. Appl. No. 13/007,518 Office Action dated Aug. 5, 2013.
U.S. Appl. No. 13/204,423 Office Action dated Dec. 5, 2012.
CN201180013558.8 Office Action dated Nov. 13, 2014 (w/English Translation).
Dalyrmple et al. A repartitioning agent to improve performance and carcass composition of broilers. Poult Sci 63(12):2376-2383 (1984).
Declaration of Dr. Kenneth Locke together with CV and data exhibits dated Feb. 24, 2014.
Drugs in Japan. Japan Drug Information Center. pp. 882-884 (2004 Ed.) (w/Partial English Translation).
EP06787329.9 Decision Rejecting Opposition dated Feb. 5, 2015.
GB1120090.4 Office Action dated Jan. 19, 2015.
Hamano et al. Combined effects of clenbuterol and various concentrations of protein on performance of broiler chickens. Br Poul Sci 39:117-122 (1998).
*Human Genome Sciences Inc.* v *Eli Lilly and Company* UKSC 51 [2011].
IL216217 Office Action date Dec. 3, 2014 (English Only).
JP2011-083171 Pre-Appeal Examination Report dated Dec. 19, 2014 (w/English translation).
JP2012-513273 Office Action dated Nov. 20, 2014 (w/English Translation).
JP2012-549145 Office Action dated Nov. 12, 2014 (w/English Translation).
Letter written by Professor Frank Greenway, M.D. to Dr. John Dobak, M.D., dated May 12, 2010.
Med. Pract. 22(4):611-615 (2005) (w/Partial English Translation).
MX/a/2011/012542 Notice of Allowance dated Dec. 16, 2014 (w/English Translation).
Nema et al. Encyclopedia of Pharmaceutical Technology pp. 1622-1645 (2007).
NZ2011336869 Office Action dated Feb. 13, 2015.
Rehfeldt et al. Effect of clenbuterol on growth, carcase and skeletal muscle characteristics in broiler chickens. Br Poul Sci 38:366-373 (1997).
Strickley. Solubilizing excipients in oral and injectable formulations. Pharm Res. 21(2):201-230 (2004).
U.S. Appl. No. 12/763,030 Office Action dated Dec. 8, 2014.
U.S. Appl. No. 13/204,423 Office Action dated Dec. 15, 2014.
U.S. Appl. No. 12/788,190 Office Action dated Mar. 4, 2015.
Zhou et al. Effects of dietary supplementation of beta 2-adrenergic agonist clenbuterol on carcase characteristics and some metabolites in ducks. Br Poul Sci 35:355-361 (1994).
CN200680031397.4 Office Action dated Feb. 4, 2015 (w/English translation).
KR10-2012-7021302 Office Action dated Feb. 24, 2015 (w/English Translation).
SG201304014-2 Written Opinion dated Feb. 2, 2015.
U.S. Appl. No. 90/013,348 Office Action dated Mar. 23, 2015.
CN201180056619.9 Office Action dated Dec. 1, 2015 (w/English translation).
EP10781245.5 Office Action dated Dec. 15, 2015.
JP2011-083171 Office Action dated Dec. 15, 2015 (w/English translation).
JP2012-095792 Pre-Trial Patentability Report dated Nov. 20, 2015 (w/English Translation).
JP2014-038412 Office Action dated Dec. 15, 2015 (w/English translation).
JP2014-052975 Office Action dated Nov. 17, 2015 (w/English translation).
PCT/US2015/052248 International Search Report and Written Opinion dated Dec. 22, 2015.
AU2011336869 Office Action dated Apr. 16, 2015.
CA2,761,744 Office Action dated Apr. 1, 2015.
CA2,786,618 Examination Report dated Jan. 16, 2015.
CN200680031397.4 Office Action dated Sep. 2, 2015 (w/English translation).
CN201080023277.6 Office Action dated Apr. 8, 2015 (w/English Translation).
CN201180013558.8 Office Action dated Jun. 2, 2015 (w/English Translation).
CN201180056619.9 Office Action dated Mar. 18, 2015(w/English Translation).
Co-pending U.S. Appl. No. 14/835,587, filed Aug. 25, 2015.
Co-pending U.S. Appl. No. 14/866,471, filed Sep. 25, 2015.
IL198184 Notice of Allowance dated Mar. 16, 2015 (w/English translation).
IL220818 Office Action dated Apr. 29, 2015 (English translation only).
JP2012-095792 Office Action dated May 19, 2015 (w/English Translation).
JP2012-549145 Office Action dated Apr. 13, 2015 (w/English Translation).
JP2013-541034 Office Action dated Sep. 24, 2015 (w/English translation).
JP2014-038412 Office Action dated Feb. 12, 2015 (w/English Translation).
JP2014-052975 Office Action dated Feb. 13, 2015 (w/English Translation).
JP2015-143281 Office Action dated Oct. 7, 2015 (English only).
KR10-2012-7021302 Office Action date Apr. 17, 2015 (w/English Translation).
KR10-2015-7018454 Office Action dated Sep. 14, 2015 (w/English translation).
Krochmal et al. Aesthetic Treatment of Central Abdominal Bulging (CAB) with LIP-202 (Salmeterol Xinafoate for Injection). J of Derm Clin Res 7 pgs (2015).
MX/a/2012008171 Office Action dated Sep. 2, 2015 (w/English translation).
Sterile Water (Water) Injection, Solution, Hospira Mar. 2007.
TW100142782 Office Action dated Aug. 25, 2015 (w/English translation).
U.S. Appl. No. 12/445,570 Office Action dated Oct. 2, 2015.
U.S. Appl. No. 12/763,030 Office Action dated May 18, 2015.
U.S. Appl. No. 13/007,518 Office Action dated Jun. 30, 2015.
U.S. Appl. No. 13/096,895 Office Action dated Jun. 26, 2012.
U.S. Appl. No. 13/303,045 Office Action dated Jun. 2, 2015.
U.S. Appl. No. 90/013,336 Ex Parte Communication and Notice of Intent to Issue Ex Parte Reexamination Certificate dated Jul. 31, 2015.
U.S. Appl. No. 90/013,336 Ex Parte Reexamination Interview Summary dated May 12, 2015.
U.S. Appl. No. 90/013,348 Ex Parte Communication and Notice of Intent to Issue Ex Parte Reexamination Certificate dated Jul. 31, 2015.
U.S. Appl. No. 90/013,348 Ex Parte Reexamination Interview Summary dated May 12, 2015.
CN200680031397.4 Board Decision dated Mar. 23, 2016 (w/English translation).
Co-pending U.S. Appl. No. 15/156,187, filed May 16, 2016.
Garcia. β2 Agonists Prolonged Action in the Treatment of Asthma in Children. Neumolgia Pediatrica pp. 96-99 (2010). Available at http://www.neumologia-pediatrica.cl (Machine translation).
JP2012-060876 Office Action dated Apr. 5, 2016 (w/English translation).
JP2013-0541034 Office Action dated Jun. 1, 2016 (w/English translation).
JP2015-060875 Office Action dated Apr. 5, 2016 (w/English translation).
KR-10-2015-7018454 Notice of Allowance dated May 16, 2016 (partial translation).
KR10-2015-7018454 Office Action dated Feb. 1, 2016 (w/English translation).
Medical Pharmacy, Japan Formulary, Ltd. Newsletter pp. 2145-2146 (2004) (English Summary).
Medical Pharmacy, Japan Formulary, Ltd. Newsletter pp. 882-884 (2004) (English Summary).
Sagara. Right and wrong of salmeterol/fluticasone propionate combination. Arerugi 55(7):794-810 (2007 English Abstract).
Therapeutics 39:100-101 (2005) (English Summary).

(56) References Cited

OTHER PUBLICATIONS

U.S. Appl. No. 13/007,518 Office Action dated Apr. 27, 2016.
U.S. Appl. No. 14/835,587 Office Action dated Feb. 8, 2016.
U.S. Appl. No. 14/866,471 Office Action dated May 20, 2016.
Vos et al. Pretibiaal myxoedeem. Nederlands Tijdschrift voor Dermatologie en Venereologie 17:71-73 (Machine translation) (2007).
CN201180013558.8 Office Action dated Aug. 16, 2016 (w/English translation).
U.S. Appl. No. 13/007,518 office Action dated Nov. 4, 2016.

* cited by examiner

SELECTIVE, LIPOPHILIC, AND LONG-ACTING BETA AGONIST MONOTHERAPEUTIC FORMULATIONS AND METHODS FOR THE COSMETIC TREATMENT OF ADIPOSITY AND CONTOUR BULGING

CROSS-REFERENCE

This patent application claims the benefit of U.S. Provisional Application Ser. No. 61/417,098 filed Nov. 24, 2010, which is incorporated by reference herein in its entirety.

BACKGROUND OF THE INVENTION

Cosmetics are substances used to enhance the appearance of the human body. Traditionally, cosmetics have included skin-care creams, lotions, powders, perfumes, lipsticks, nail polish, eye and facial makeup, and so forth. The United States Food and Drug Administration (the FDA), which regulates cosmetics in the United States, broadly views a cosmetic as a substance that is intended to be applied to the human body for cleansing, beautifying, promoting attractiveness, or altering the appearance without significantly affecting the body's structure or functions.

Accumulation of fat stores in humans can occur unevenly in the body, which to certain individuals is considered to be a cosmetic blemish. For example, some persons may accumulate fat predominantly in visceral areas while others predominately in the subcutaneous tissue. Gender differences may also be apparent with women accumulating fat in the thighs and lateral buttocks and males in the waist. Women may accumulate fatty deposits of the thighs, which have a rumpled or "peau d' orange" appearance, resulting in a condition referred to as cellulite. Cellulite may be related to skin architecture which allows subdermal fat herniation, sometimes referred to as adipose papillae.

SUMMARY OF THE INVENTION

The subject matter described herein provides cosmetic and pharmaceutical monotherapy formulations for the reduction of subcutaneous adiposity in humans. Specifically, described herein are subcutaneous and transcutaneous pharmaceutical and cosmetic monotherapy formulations and methods of treatment for regional adiposity. Also provided herein are pharmaceutical and/or cosmetic formulations for, in certain situations, reducing regional fat deposits in a subject.

In one aspect, provided herein are injectable formulations for regional adiposity reduction comprising: (a) active ingredient that consists essentially of an adipose tissue-reducing amount of one or more lipophilic long-acting selective beta-2 adrenergic receptor agonists, or salts, solvates, or polymorphs thereof; and (b) one or more subcutaneously acceptable inactive ingredients. In another aspect, provided herein is a cosmetic method for reducing adiposity in a human patient comprising subcutaneously administering a formulation suitable for subcutaneous injection comprising: (a) active ingredient that consists essentially of a cosmetically effective adipose tissue-reducing amount of one or more lipophilic long-acting selective beta-2 adrenergic receptor agonists, or salts, solvates, or polymorphs thereof; and (b) one or more subcutaneously acceptable inactive ingredients. In yet another aspect, provided herein is a cosmetic method for inducing lipolysis in adipose tissue of a human patient comprising subcutaneously administering a formulation suitable for subcutaneous injection comprising: (a) active ingredient that consists essentially of a cosmetically effective adipose tissue-reducing amount of one or more lipophilic long-acting selective beta-2 adrenergic receptor agonists, or salts, solvates, or polymorphs thereof; and (b) one or more subcutaneously acceptable inactive ingredients. In a further aspect, provided herein is a method for the aesthetic treatment of body contour defects such as abdominal bulging in a human patient comprising subcutaneously administering a formulation suitable for subcutaneous injection comprising: (a) active ingredient that consists essentially of a cosmetically effective adipose tissue-reducing amount of one or more lipophilic long-acting selective beta-2 adrenergic receptor agonists, or salts, solvates, or polymorphs thereof; and (b) one or more subcutaneously acceptable inactive ingredients. In an aspect provided is a method for aesthetic treatment of cheek contour defect in a human patient by contacting a targeted fat deposit in the cheek with a composition comprising: (a) active ingredient that consists essentially of a cosmetically effective adipose tissue-reducing amount of one or more lipophilic long-acting selective beta-2 adrenergic receptor agonists, or salts, solvates, or polymorphs thereof; and (b) one or more subcutaneously acceptable inactive ingredients. In another aspect, provided herein are compositions, formulations, methods, and systems for treating thyroid eye disease by contacting a targeted fat deposit in the eye with a composition comprising: (a) active ingredient that consists essentially of an adipose tissue-reducing amount of one or more lipophilic long-acting selective beta-2 adrenergic receptor agonists, or salts, solvates, or polymorphs thereof; and (b) one or more subcutaneously acceptable inactive ingredients.

DETAILED DESCRIPTION OF THE INVENTION

Figure 1:
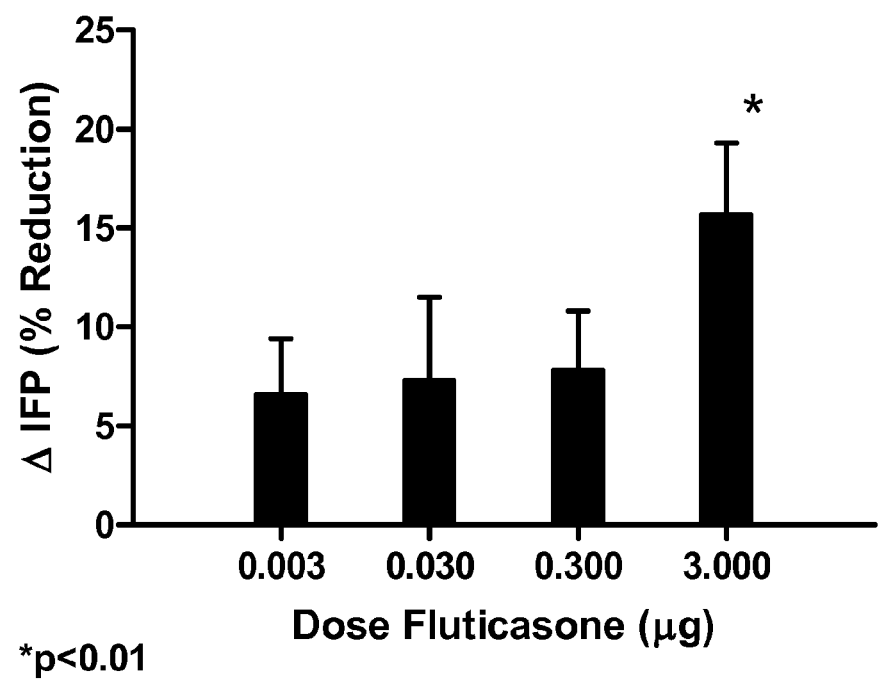
FIG. 1 illustrates effects of salmeterol xinafoate on change in inguinal fat pad weight ($\Delta$IFP) (% reduction; mean$\pm$SEM) following SC injection into the fat pad.

Adipose tissue is the primary energy storage tissue of the body. Fat cells, or adipocytes, store this energy in the form of triglycerides. Triglycerides are mobilized from fat stores to provide caloric energy to the body through hormonal induction of triglyceride hydrolysis. This process releases free or non-esterified fatty acids and glycerol into the blood for use by other body tissues. The breakdown of triglycerides from fat store is referred to as lipolysis. Growth of new adipocytes also occurs, which is referred to as adipogenesis. Primary neurotransmitters that control lipolysis in the body are the catecholamines epinephrine and norepinephrine. Adipose tissue has beta-1, 2, and 3 adrenergic receptors and alpha-2 adrenergic receptors. Binding of beta-adrenergic receptor agonists ("beta-adrenergic agonists") to beta-adrenergic ("beta") receptors in adipose tissue results in adipocyte lipolysis. Beta-adrenergic receptor activation also inhibits adipogenesis. In humans, beta-2 receptors are the most abundant on fat cell surfaces and the primary mediator of beta-adrenergic receptor-stimulated lipolysis. Stimulation of lipolysis by beta-adrenergic agonists is mediated by adenylate cyclase and increased formation of cyclic adenosine monophosphate (cyclic AMP, cAMP).

Long-acting beta-2 adrenergic receptor agonists, such as salmeterol and formoterol, reduce regional fat deposits or adipose tissue regions by binding to beta receptors, resulting in adipocyte lipolysis. The use of long-acting beta-2 adrenergic receptor agonists, however, carries with it possible side effects. For example, use of long-acting beta-2 adrenergic receptor agonists may result in cardiovascular problems such as angina, hypertension or hypotension, tachycardia, palpitations, and arrhythmias. Thus, while long-acting beta-2 adrenergic receptor agonists may reduce regional fat deposits and adipose tissue regions they may also cause increased heart rate and palpitations.

It has been found that certain lipophilic long-acting selective beta-2 adrenergic agonists administered subcutaneously in appropriate amounts reduce regional fat deposits with limited systemic exposure compared to other long-acting beta-2 adrenergic agonists. One possible reason for this result is that the lipophilic nature of certain long-acting beta-2 adrenergic receptor agonists allows selective partitioning into the adipose tissue relative to plasma. The lipophilicity of certain long-acting beta-2 adrenergic receptor agonist into the subcutaneous adipose tissue contributes, at least in part, to providing relatively low levels of the agonist systemically. Appropriate amounts of the lipophilic long-acting beta-2 adrenergic receptor agonists described herein administered via subcutaneous or transcutaneous injection may provide therapeutic effectiveness in reducing regional fat deposits and/or adipose tissue with a reduced risk of producing cardiovascular side effects. Indeed, the formulations described herein are prepared to be administered subcutaneously or transcutaneously, and not systemically. Accordingly, the formulations and methods of treatment described herein are designed to reduce subcutaneous adipose tissue which is distinct from visceral (systemic) fat.

Glossary of Certain Terminology

"Cosmetically effective" as used herein, refers to a sufficient amount of an agent (e.g., a selective, long-acting, and long-acting beta-2 agonist) which will improve the cosmetic appearance at the localized site of treatment. A "cosmetically effective" amount of a selective, lipophilic, and long-acting beta-2 agonist is an amount effective to achieve a cosmetically desirable improvement. It is to be understood that a "cosmetically effective" amount can vary from subject to subject, due to numerous factors including for example age, weight, general condition of the subject, the condition being treated, the severity of the condition being treated, and the judgment of the prescribing physician.

As used herein, an "aesthetic treatment" or "cosmetic treatment" refers to any treatment carried out for the purposes of improving the visual appearance. A method for aesthetic treatment refers to a method of improving the visual appearance at the localized site of treatment by providing an effective amount of an agent (e.g., a selective, long-acting, and long-acting beta-2 agonist) which will improve the cosmetic appearance at the localized site of treatment. As used herein, the aesthetic treatment of a body contour defect refers to any treatment carried out to achieve a more natural or cosmetically desirable body shape.

As used herein an "adipose tissue-reducing" amount refers to a sufficient amount of the lipophilic long-acting beta-2 adrenergic receptor agonist needed to reduce adipose tissue. It is to be understood that the amount sufficient to decrease the adipose tissue will vary from subject to subject due to variation in metabolism of the lipophilic long-acting beta-2 adrenergic receptor agonist, with age, weight, general condition of the subject, the severity of the condition being treated, and the judgment of the prescribing physician.

As used herein, "Thyroid Eye Disease" or "Graves' Opthamolopathy" or "Thyroid-associated orbitopathy" or "Grave's orbitopathy" refers to an eye condition that is characterized by one or more of: swelling in the orbital tissues; protrusion of one or both eyeballs—also known as exophthalmos; proptosis, in which the eyes appear to bulge outward. Without being limited by theory, it is believed the clinical symptoms and signs of Thyroid Eye Disease can be explained mechanically by the increase in tissue volume evident within the bony orbit. The expanded orbital tissues cause forward displacement of the globe and impairment of venous and lymphatic outflow from the orbit. These changes, combined with the local production of cytokines and other mediators of inflammation, result in proptosis, periorbital edema, conjunctival erythema and/or chemosis.

A formulation that is "substantially free" of a specific compound or substance contains an amount that is equal to or less than a trace or therapeutically or cosmetically insignificant amount of the specific compound or substance. For example, a formulation that is "substantially free" of a glucocorticosteroid contains an amount that is equal to or less than a trace of therapeutically or cosmetically insignificant amount of glucocorticosteroids.

As described herein a "reduced or minimized risk of producing cardiovascular side effects" amount refers to an amount of the lipophilic long-acting beta-2 adrenergic receptor agonist used which does not result in clinically significant cardiovascular side effects. It is to be understood that the amount used will vary from subject to subject due to variation in metabolism of the lipophilic long-acting beta-2 adrenergic receptor agonist, with age, weight, general condition of the subject, the severity of the condition being treated, and the judgment of the prescribing physician.

"Plasma concentration" refers to the concentration of a substance such as a therapeutic agent, in blood plasma of a subject. It is understood that the plasma concentration of a therapeutic agent may vary many-fold between subjects, due to variability with respect to metabolism of therapeutic agents. In accordance with one aspect, the plasma concentration of a long-acting beta-2 adrenergic receptor agonist varies from subject to subject. Likewise, in some embodiments, values such as maximum plasma concentration ($C_{max}$) or time to reach maximum plasma concentration ($T_{max}$), or total area under the plasma concentration time curve (AUC) varies from subject to subject. Due to this variability, the amount necessary to constitute "a therapeutically effective amount" of a lipophilic long-acting beta-2 adrenergic receptor agonist varies from subject to subject. It is understood that in some embodiments, when mean plasma concentrations are disclosed for a population of subjects, these mean values include substantial variation.

"Pharmacodynamics" refers to the factors that determine the biologic response observed relative to the concentration of drug at a site of action.

"Pharmacokinetics" refers to the factors that determine the attainment and maintenance of the appropriate concentration of drug at a site of action.

A "measurable plasma concentration" or "measurable plasma concentration" describes the blood plasma or blood plasma concentration, typically measured in mg, µg, or ng of therapeutic agent per mL, dL, or L of blood plasma, of a therapeutic agent that is absorbed into the bloodstream after administration. One in the field would be able to measure the plasma concentration or plasma concentration of a lipophilic long-acting beta-2 adrenergic receptor agonist.

Some embodiments comprise optically pure isomers of the lipophilic beta-adrenergic agonist(s), which improve lipolysis and adipogenesis inhibition and reduce the risk of producing potential cardiovascular side effects. In some embodiments, these optically pure isomers allow formulations comprising larger loadings of an active ingredient, for example, by eliminating one or more isomers with no physiological effect, a lesser a physiological effect, a negative effect, and/or an undermined physiological effect. Removing the undesired bounds of a racemic mixture isolates the active isomer, or eutomer, thereby allowing more eutomer to be loaded in a give formulation by removing the inactive components.

Two stereogenic centers in a molecule generally generate two diastereomers, referred to herein as (R*,R*) and (R*, S*), and their enantiomers. Diastereomers are stereoisomers that are not enantiomers, that is, the mirror image of one diastereomer is not superimposable on another diastereomer. Enantiomers are stereoisomers that are mirror images of each other. A racemate is a 1:1 mixture of enantiomers. The enantiomers of the (R*,R*) diastereomers are referred to as the (R,R) and (S,S) enantiomers, which are mirror images of each other and therefore share some chemical and physical properties, for example melting points. Similarly, the (R,S) and (S,R) isomers are enantiomers of the (R*,S*) enantiomer. For example, some embodiments comprise optically pure isomers of lipophilic beta-2 agonists, for example, (R)-salmeterol.

Additionally, in some embodiments, long-acting selective beta-2 agonists are lipophilic, thereby providing a pharmaceutical and/or cosmetic formulation with activity in fat tissue. In some embodiments, the lipophilic agonist is salmeterol. In further embodiments, the lipophilicity of salmeterol provides prolonged exposure to the adipose tissue. In some embodiments, the agent is not salmeterol, but has a similar lipophilicity to salmeterol.

Salmeterol has high lipid solubility, compared to other long-acting beta-2 adrenergic receptor agonists, such as for example, formoterol, which extends its residence time in the adipose tissue and/or in one or more adipose cells. Some embodiments of the subcutaneous formulation comprise a highly lipophilic beta-adrenergic agonist, which reduces or eliminates the need for a sustained or controlled release carrier due to partitioning and sequestration in the adipose tissue thereby prolonging the treatment effect. In some embodiments, lipophilic beta-adrenergic agonists with an oil-water partition coefficient of at least about 1000 or at least about 10,000 to 1 are used. For example, salmeterol is at least 10,000 times more lipophilic than albuterol, a short-acting hydrophilic beta-adrenergic agonist.

A "treatment period" is defined as the period of time the patient is under a physician's care or direction, which may vary from patient to patient, and may be dependent on metabolism of the lipophilic long-acting beta-2 adrenergic receptor agonist administered to the patient, age, weight, general condition of the subject, the severity of the condition being treated, and the judgment of the prescribing physician. In some embodiments, the treatment period comprises between 1 week and 52 weeks, longer than 52 weeks, or any amounts of weeks between 1 and 52.

A "weekly dose" is the total amount of active ingredient administered to a patient during a single week. For example, in situations with more than a single administration occurs during a week, the weekly dose is the total amount of active ingredient provided to the patient in each administration that occurs during the week.

A "periodic dose" is the frequency at which a dose is administered to a patient during a period.

A "single session dose" is the total amount of active ingredient administered to a patient during a single visit for treatment by a healthcare professional or, in situations of self-administration, a single session dose is the total amount of active ingredient administered to the patient by self-administration in a single session.

In some embodiments, a single session dose is divided into smaller amounts and administered to a patient in one or more "sub-doses." In some embodiments, each "sub-dose" is subcutaneously delivered to a patient by injection, e.g., using a syringe or is administered to the patient transcutaneously.

The phrases "patient" and "subject" are used interchangeably herein. In some embodiments, the patient or subject is a human. In further or additional embodiments, the patient or subject is an animal. In some embodiments, the animal is a human, a common household pet, including for example a cat or a dog, or a species of the animal kingdom. In some embodiments, the patient is a non-murine animal.

Lipophilic, Selective, and Long-Acting Beta-2 Adrenergic Receptor Agonists

In one aspect, provided herein are pharmaceutical and/or cosmetic formulations suitable for subcutaneous or transcutaneous administration and methods of treatment comprising subcutaneously or transcutaneously administering to a patient a pharmaceutical and/or cosmetic formulation (including all of the methods of treatment described herein). In some embodiments, the pharmaceutical and/or cosmetic formulation comprises an injectable formulation for regional adiposity reduction consisting essentially of: (a) active ingredient that consists essentially of an adipose tissue-reducing amount of one or more lipophilic long-acting selective beta-2 adrenergic receptor agonists, or salts, solvates, or polymorphs thereof; and (b) one or more subcutaneously acceptable inactive ingredients. In further or additional embodiments, the formulations provided herein comprise an injectable formulation for regional adiposity reduction consisting of: (a) active ingredient that consists essentially of an adipose tissue-reducing amount of one or more lipophilic long-acting selective beta-2 adrenergic receptor agonists, or salts, solvates, or polymorphs thereof; and (b) one or more subcutaneously acceptable inactive ingredients. In further or additional embodiments, the formulations provided herein comprise an injectable formulation for regional adiposity reduction comprising: (a) active ingredient that consists essentially of an adipose tissue-reducing amount of one or more lipophilic long-acting selective beta-2 adrenergic receptor agonists, or salts, solvates, or polymorphs thereof; and (b) one or more subcutaneously acceptable inactive ingredients. In specific embodiments of the methods and formulations described herein, the injectable formulations are substantially free of glucocorticosteroids.

In some embodiments, provided herein are pharmaceutical and/or cosmetic formulations, and methods of treatment, comprising administration of the pharmaceutical and/or cosmetic formulations to a patient, wherein the formulation is suitable for subcutaneous administration. In further or additional embodiments, the pharmaceutical and/or cosmetic formulation is suitable for transcutaneous administration.

In some embodiments, the pharmaceutical and/or cosmetic formulation comprises a lipophilic long-acting selective beta-2 adrenergic receptor agonist, or a salt, optical isomer, racemate, solvate, or polymorph thereof. For example, in some embodiments, the lipophilic long-acting selective beta-2 adrenergic receptor agonist is salmeterol (including various salt forms such as xinafoate). In further or additional embodiments the lipophilic long-acting selective beta-2 adrenergic receptor agonist is formoterol (including various salt forms such as fumarate and furoate).

In other embodiments, the pharmaceutical and/or cosmetic formulation consists essentially of a lipophilic long-acting selective beta-2 adrenergic receptor agonist, or a salt, optical isomer, racemate, solvate, or polymorph thereof.

In one aspect, provided herein are pharmaceutical and/or cosmetic formulations suitable for subcutaneous or transcutaneous administration comprising a lipophilic long-acting selective beta-2 adrenergic receptor agonist, including, for example, salmeterol or 2-(hydroxymethyl)-4-{1-hydroxy-2-[6-(4-phenylbutoxy)hexylamino]ethyl}phenol, or its salts, optical isomers, racemates, solvates or polymorphs thereof and when used in the appropriate amounts and administered transcutaneously or subcutaneously, provides a therapeutic effect for reducing regional fat deposits and/or adipose tissue with limited systemic exposure, and consequently, a reduced risk of producing cardiovascular side effects. In one embodiment is a subcutaneous or transcutaneous preparation for the reduction of adipose tissue and/or the reduction in regional fat deposits comprising an adipose tissue-reducing amount of a lipophilic long-acting selective beta-2 adrenergic agonist wherein the formulation does not result in high systemic levels when administered subcutaneously or transcutaneously. In another embodiment, the lipophilic long-acting selective beta-2 adrenergic receptor agonist is salmeterol. In yet another embodiment, the agonist is a polymorph of salmeterol, such as for example, polymorph I and II. Such subcutaneous or transcutaneous preparations provide the required tissue concentration of salmeterol needed to reduce adipose tissue and/or reduce regional fat deposits with a minimized or reduced risk of producing the side effects typically associated with the administration of beta-2 adrenergic receptor agonists, including other long-acting beta-2 adrenergic receptor agonists. Additionally, the use of salmeterol in a subcutaneous or transcutaneous preparation provides therapeutically effective dosages without producing relatively high systemic levels found when using other long-acting beta-2 adrenergic receptor agonists, such as for example, formoterol.

receptor agonist is selective for the beta-2 adrenergic receptor. In further or additional embodiments, the beta-2 adrenergic receptor agonist is lipophilic. In further or additional embodiments, the beta-2 adrenergic receptor agonist is long-acting.

In some embodiments, the beta-2 adrenergic receptor agonist is bambuterol, bitolterol, broxaterol, carbuterol, carmoterol, clenbuterol, ibuterol, sulfonterol, isoproterenol, trimetoquinol, formoterol, desformoterol, hexoprenaline, ibuterol, indacaterol, isoetharine, isoprenaline, isoproterenol, levalbuterol, metaproterenol, picumeterol, pirbuterol, procaterol, reproterol, rimiterol, salbutamol, salmeterol, sulfonterol, terbutaline, trimetoquinol, tulobuterol, TA-2005 (8-hydroxy-5-((1R)-1-hydroxy-2-(N—((1R)-2-(4-methoxyphenyl)-1-methylethyl-)amino)ethyl)-carbostyril hydrochloride), QAB-149 (Novartis), TA-2005, GSK-159797, or GSK-642444, or a salt, optical isomer, racemate, solvate, or polymorph thereof.

In some embodiments, the beta-2 adrenergic receptor agonist is long-acting and is selected from salmeterol, formoterol, bambuterol, or clenbuterol. In further or additional embodiments, the beta-2 adrenergic receptor agonist is a specific type of long-acting that is ultra long-acting. In some embodiments, the ultra long-acting beta-2 adrenergic receptor agonist is selected from indacaterol, carmoterol, QAB-149, CHF-4226, TA-2005, GSK-159797, and GSK-642444.

In some embodiments, provided herein are pharmaceutical and/or cosmetic formulations comprising an active ingredient consisting essentially of an adipose tissue-reducing amount of a lipophilic long-acting selective beta-2 adrenergic receptor agonist or a salt, optical isomer, racemate, solvate, or polymorph thereof and at least one subcutaneously or transcutaneously acceptable inactive ingredient. In one embodiment, the lipophilic long-acting selective beta-2 adrenergic receptor agonist selectively partitions into adipose tissue relative to plasma.

In another embodiment, the lipophilic long-acting selective beta-2 adrenergic receptor agonist is salmeterol (±2-(hydroxymethyl)-4-[1-hydroxy-2-[6-(4-phenylbutoxy) hexylamino]ethyl]-phenol, CAS Reg. No. 94749-08-3, shown below as compound 1).

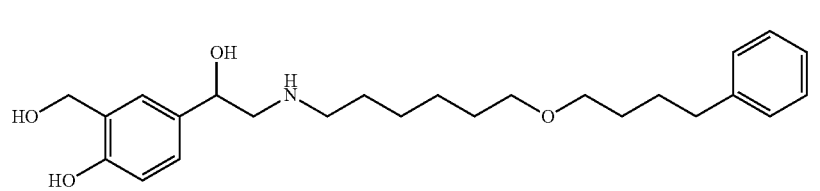

In another aspect, provided herein are pharmaceutical and/or cosmetic formulations suitable for subcutaneous or transcutaneous administration and methods of treatment comprising subcutaneously or transcutaneously administering to a patient a pharmaceutical and/or cosmetic formulation (including all of the methods of treatment described herein) wherein the pharmaceutical and/or cosmetic formulation comprises a beta-2 adrenergic receptor agonist.

In some embodiments, provided herein are pharmaceutical and/or cosmetic formulations and methods of treatment comprising a beta-2 adrenergic receptor agonist, or a salt, optical isomer, racemate, solvate, or polymorph thereof, that is characterized by at least one of the following properties: lipophilic; selective for the beta-2 adrenergic receptor; and long-acting. In some embodiments, the beta-2 adrenergic In other embodiments, the lipophilic, long-acting, selective beta-2 agonist is a polymorph of salmeterol. In a further embodiment, the polymorph is polymorph I or II. In further embodiments, the formulation uses a mixture of salmeterol polymorphs. In yet another embodiment, the salt of the lipophilic long-acting selective beta-2 adrenergic receptor agonist is a xinafoate salt. In some embodiments, the lipophilic long-acting selective beta-2 adrenergic receptor agonist is salmeterol xinafoate.

Some embodiments provide adrenergic modulation through the use of pharmaceutical and/or cosmetic compositions comprising an adipose tissue-reducing and lipophilic, long-acting selective beta-2 receptor agonist active ingredient administered subcutaneously or transcutaneously, either alone (as single agent therapy), or in combination with at least a second active ingredient (as a combination therapy). Thus, in some embodiments, the pharmaceutical and/or cosmetic formulations (and corresponding methods of treatment provided herein) consist essentially of a lipophilic, long-acting, selective beta-2 agonist, for example, salmeterol, physiologically acceptable salts, optical isomers, racemates, solvates, polymorphs, or combinations thereof, wherein the formulation is suitable for subcutaneous or transcutaneous administration. In further or additional embodiments, the pharmaceutical and/or cosmetic formulation comprises a lipophilic, long-acting, selective beta-2 agonist, for example, salmeterol, physiologically acceptable salts, optical isomers, racemates, solvates, polymorphs, or combinations thereof, and at least a second active ingredient, wherein the formulation is suitable for subcutaneous or transcutaneous administration.

Lipophilic, long-acting, selective beta-2 agonists, for example, salmeterol are used in some embodiments. In other embodiments, salts, optical isomers, racemates, polymorphs, and/or solvates of beta-2 agonists have the desired activity and are accordingly provided for herein. Unless otherwise specified, references to an active ingredient, for example, to salmeterol, include the compound itself as well as a physiologically acceptable analogs, salts, optical isomers, racemates, polymorphs, solvates, or combinations thereof.

In some embodiments, salmeterol is used in the compositions and methods described herein. Depending on the tissue, salmeterol may exhibit partial agonist activity, which is believed to reduce receptor desensitization and may limit arrestin signaling leading to less receptor down-regulation. In some embodiments, salmeterol is present as a physiologically acceptable salt, optical isomer, racemate, solvate, and/or polymorph thereof. Suitable physiologically acceptable salts of salmeterol include, but are not limited to acid addition salts derived from inorganic and organic acids, such as the hydrochloride, hydrobromide, sulfate, phosphate, maleate, tartrate, citrate, benzoate, 4-methoxybenzoate, 2-hydroxybenzoate, 4-hydroxybenzoate, 4-chlorobenzoate, p-toluenesulphonate, methanesulphonate, ascorbate, salicylate, acetate, fumarate, succinate, lactate, glutarate, gluconate, tricarballylate, hydroxynaphthalenecarboxylate, 1-hydroxy-2-naphthalenecarboxylate, 3-hydroxy-2-naphthalenecarboxylate, oleate, combinations thereof, and the like. In some embodiments, salmeterol is provided as the 1-hydroxy-2-naphthalene carboxylate salt (hydroxynaphthoate, also known as xinafoate).

Dosing

In some embodiments, long-term exposure of adipose tissue to adrenergic agents, particularly beta-adrenergic receptor agonists, results in receptor desensitization through receptor phosphorylation and sequestration. These effects limit the ability of an adrenergic modulating composition to treat adipose tissue and result in tachyphylaxis, a condition in which the body experiences a rapidly decreasing response to the agonist following administration of the initial doses, to the desired lipolytic and anti-adipogenesis effect. Consequently, in certain situations with long-term exposure of adipose tissue to beta-adrenergic receptor agonists, the therapeutic effect with the beta-adrenergic receptor agonists is short-lived.

Repeated administration of short-acting beta-2 agonists often result in tachyphylaxis. However, salmeterol, exhibits partial beta-2 receptor agonist activity in some systems that may reduce the desensitization that occurs with continuous exposure of adipocytes to full adrenergic receptor agonists. Compared with short-acting beta-2 agonists, lipolysis also occurs for a longer time after administration because lipophilic, long-acting selective beta-2 agonists have longer half-lives. The combination of longer half-lives and activities reduces the required frequency and total dosage of administration of the pharmaceutical and/or cosmetic compositions provided herein. Consequently, in some embodiments, daily administration or more than once daily administration of the composition is not required. In some embodiments, provided herein are subcutaneously or transcutaneously administered adipose tissue-reducing lipophilic, long-acting selective beta-2 agonists which exhibit greater selectivity for beta-2 receptors, permitting substantially similar therapeutic effects with less selective beta-2 agonists at a lower dosage and/or less frequent dosage. Further the more selective beta-2 activity can limit cardiac and other systemic side effects, which in the case of cardiac side effects, is often induced by beta-1 receptor stimulation in the heart. In some embodiments, provided are subcutaneous or transcutaneous formulations of lipophilic, long-acting beta-2 agonists which provide selectivity for beta-2 receptors while reducing the risk of producing cardiac or systemic side effects.

Provided herein are pharmaceutical and/or cosmetic formulations that are suitable for subcutaneous or transcutaneous administration.

In some embodiments, the pharmaceutical and/or cosmetic formulations provided herein are suitable for subcutaneous injection, and provide for a volume of up to about 20 mL (including, e.g., about 0.1 mL, about 0.3 mL, about 0.5 mL, about 0.7 mL, about 1.0 mL, about 1.1 mL, about 1.5 mL, about 2 mL, about 2.5 mL, about 3 mL, about 3.5 mL, about 4 mL, about 5 mL, about 6 mL, about 7 mL, about 8 mL, about 9 mL, or any other volume from about 0.1 mL to about 20 mL) of an excipient compatible with subcutaneous administration. In some embodiments, the volume for injection is provided in a range that is between about 0.1 mL to about 20 mL, about 0.2 mL to about 15 mL, about 0.3 mL to about 10 mL, about 0.4 mL to about 7 mL, about 0.5 mL to about 5 mL, about 0.6 mL to about 4 mL, about 0.7 mL to about 3 mL, about 0.8 mL to about 2 mL, or about 1 mL. In some embodiments, the excipient concentration is kept below 1% (e.g., about 0.05%, about 0.2%, about 0.3%, about 0.4%, about 0.5%, about 0.6%, about 0.8%, or any other concentration from about 0.05% to less than about 1%. In specific embodiments, the excipient concentration is between about 0.01% to about 1%, about 0.05% to about 0.9%, about 0.2% to about 0.8%, about 0.3% to about 0.7%, about 0.4% to about 0.6%, or about 0.5%.

Periodic Dosing Schedule

Another aspect of the formulations and methods of treatment provided herein is a periodic dosing schedule. A periodic dose is the frequency at which a single session dose is administered to a patient during a period. For example, in some embodiments, the periodic dose is once per week, and hence in these situations a patient will receive a single session dose once per week. In further or additional embodiments, the periodic dose is 2-7 times per week (including any interval between 2 and 7), 3-6 times per week (including any interval between 3 and 6), or 4-5 days per week. In some embodiments, the periodic dose is 1-4 times per month (including any interval between 1 and 4), 2-3 times per month, or once or twice per month. In some embodiments, the periodic dose is 1-52 times per year (including any interval between 1 and 52).

In some situations where the periodic dose is twice per week, the patient will receive the single session doses in two separate halves (that are about equal or unequal) during the week. Similarly, in some situations where the periodic dose is seven times per week, the amount of active ingredient administered to the patient for each single session dose compared to what is provided herein is divided by seven. As another example, in certain situations where the periodic dose is once per month, the patient will receive a single session dose per month at four times the amount that is provided herein.

Session Dose

An additional aspect of the formulations and methods of treatment provided herein is session dosing. A single session dose is the total amount of active ingredient administered to a patient during a single visit for treatment by a healthcare professional or, in situations of self-administration, it is the amount of active ingredient administered to the patient by self-administration in a session. The single session dose amounts provided herein are based on a once per week periodic dose, and the amounts can be adjusted for a different periodic dose than once per week as provided herein.

In one aspect, including certain methods of treatment comprising administration of the pharmaceutical and/or cosmetic formulations described herein, provided are pharmaceutical and/or cosmetic formulations wherein a lipophilic long-acting selective beta-2 adrenergic receptor agonist is provided in a single session dose that is less than about 20 μg of the lipophilic long-acting selective beta-2 adrenergic receptor agonist, or a salt, optical isomer, racemate, solvate, or polymorph thereof. In some embodiments, the lipophilic, long-acting selective beta-2 agonist is salmeterol, or a salt, optical isomer, racemate, solvate, or polymorph thereof. In further embodiments, the lipophilic, long-acting selective beta-2 agonist is salmeterol xinafoate. In further or additional embodiments, the salmeterol xinafoate is administered in a periodic dose that is once per week, and is administered to a patient in single session dose as provided for herein.

In some embodiments, the single session dose of salmeterol xinafoate is administered once per week in an amount between about 20 μg and about 5 ng, between about 20 μg and about 25 ng, between about 20 μg and about 50 ng, between about 20 μg and about 75 ng, between about 20 μg and about 100 ng, between about 20 μg and about 125 ng, between about 20 μg and about 150 ng, between about 20 μg and about 175 ng, between about 20 μg and about 200 ng, between 20 μg and about 225 ng, between about 20 μg and about 250 ng, between about 20 μg and about 275 ng, between about 20 μg and about 300 ng, between about 20 μg and about 325 ng, between about 19 μg and about 350 ng, between about 19 μg and about 375 ng, between about 18 μg and about 400 ng, between about 18 μg and about 425 ng, between about 18 μg and about 450 ng, between about 18 μg and about 475 ng, between about 18 μg and about 500 ng, between about 17 μg and about 525 ng, between about 17 μg and about 550 ng, between about 17 μg and about 575 ng, between about 17 μg and about 600 ng, between about 17 μg and about 625 ng, between about 17 μg and about 650 ng, between about 16 μg and about 675 ng, between about 15 μg and about 700 ng, between about 14 μg and about 725 ng, between about 13 μg and about 750 ng, between about 13 μg and about 775 ng, between about 13 μg and about 800 ng, between about 12 μg and about 825 ng, between about 11 μg and about 850 ng, between about 10 μg and about 875 ng, between about 9 μg and about 900 ng, between about 8 μg and about 920 ng, between about 7 μg and about 940 ng, between about 6 μg and about 950 ng, between about 5 μg and about 960 ng, between about 4 μg and about 980 ng, or between about 3 μg and about 1 μg. In some embodiments, a lipophilic, long-acting selective beta-2 agonist to be administered is salmeterol and an adipose tissue-reducing amount of salmeterol to be administered is less than about 5 μg per week.

In specific embodiments, provided are pharmaceutical and/or cosmetic formulations that are formulated to provide a daily dose of a lipophilic, long-acting selective beta-2 agonist. In some embodiments, a lipophilic, long-acting selective beta-2 agonist to be administered is salmeterol and an adipose tissue-reducing amount of salmeterol to be administered is about 0.001 μg/day to about 1000 μg/day, e.g., about 0.1 μg/day to about 100 μg/day, about 1 μg/day to about 100 μg/day, about 10 μg/day to about 100 μg/day, about 50 μg/day to about 100 μg/day, or any other dose of salmeterol from about 0.001 μg/day to about 1000 μg/day. In some embodiments, a lipophilic, long-acting selective beta-2 agonist to be administered is salmeterol and an adipose tissue-reducing amount of salmeterol to be administered is a daily dose that provides less than about 5 μg per week.

Sub-Dosing

In certain situations, the single session dose is administered to the patient in sub-doses (e.g., by subcutaneous injection, transcutaneous application, or otherwise). Accordingly, in another aspect, including certain methods of treatment comprising administration of the pharmaceutical and/or cosmetic formulations described herein, provided are pharmaceutical and/or cosmetic formulations wherein a lipophilic long-acting selective beta-2 adrenergic receptor agonist is provided in at least two sub-doses. In some embodiments, all of the sub-doses are provided to a patient in a single session during a single week. In further or additional embodiments, including certain methods of treatment comprising administration of the pharmaceutical and/or cosmetic formulations described herein, the active ingredient is provided in at least two sub-doses whereby all of the sub-doses are provided to a patient in a single session during a single week. In still further embodiments, at least at least two sub-doses are provided to a patient.

In some embodiments, one or more sub-dose is provided to a patient wherein each sub-dose is a single injection of a fluid comprising a lipophilic long-acting selective beta-2 adrenergic receptor agonist. For example, in some embodiments, provided herein are pharmaceutical and/or cosmetic formulations and methods of treatment comprising administration of a pharmaceutical and/or cosmetic formulation wherein a lipophilic long-acting selective beta-2 adrenergic receptor agonist is provided to a patient in about a single sub-dose, at least about two sub-doses, at least about three sub-doses, at least about four sub-doses, at least about five sub-doses, at least about six sub-doses, at least about seven sub-doses, at least about eight sub-doses, at least about nine sub-doses, at least about 10 sub-doses, at least about 11 sub-doses, at least about 12 sub-doses, at least about 13 sub-doses, at least about 14 sub-doses, at least about 15 sub-doses, at least about 16 sub-doses, at least about 17 sub-doses, at least about 18 sub-doses, at least about 19 sub-doses, at least about 20 sub-doses, at least about 21 sub-doses, at least about 22 sub-doses, at least about 23 sub-doses, at least about 24 sub-doses, at least about 25 sub-doses, at least about 26 sub-doses, at least about 27 sub-doses, at least about 28 sub-doses, at least about 29 sub-doses, at least about 30 sub-doses, at least about 31 sub-doses, at least about 32 sub-doses, at least about 33 sub-doses, at least about 34 sub-doses, at least about 35 sub-doses, or more than about 35 sub-doses. In further or additional embodiments, a lipophilic long-acting selective beta-2 adrenergic receptor agonist is provided to a patient in about a 1 to about 35 sub-doses, about 2 to about 32 sub-doses, in about 3 to about 30 sub-doses, in about 5 to about 28 sub-doses, in about 7 to about 27 sub-doses, in about 9 to about 26 sub-doses, in about 11 to about 25 sub-doses, in about 12 to about 24 sub-doses, in about 14 to about 23 sub-doses, in about 16 to about 22 sub-doses, in about 17 to about 21 sub-doses, or in about 18 to about 20 sub-doses.

In some embodiments, each sub-dose is administered to a patient in an equal amount. For example, in some situations where the single session dose is about 20 μg of salmeterol xinafoate that is delivered to the patient in 20 sub-doses, each sub-dose contains about 1 μg of salmeterol xinafoate. In other situations, the single session dose is about 500 ng and is delivered to the patient in 22 sub-doses and each sub-dose contains about 22 or 23 ng of salmeterol xinafoate. Still in further situations, a prescribing physician may administer, or the patient may self-administer, sub-doses in amounts that are not equal but vary in amount with respect to each sub-dose that is administered.

In some embodiments, at least two sub-doses of salmeterol xinafoate, as described herein, are administered to a patient in a single session dose via subcutaneous injection to the abdominal region of the patient. In some of these embodiments, each sub-dose is applied to a patient about 2-6 cm away from a closest second sub-dose. In further embodiments, each sub-dose is applied to a patient about 4 cm away from a closest second sub-dose.

In some embodiments, a sub-dose is administered, for example by subcutaneous or transcutaneous injection, to areas of non-visceral fat deposits on a subject, including for example subcutaneous fat. In some embodiments for which the formulations described herein are useful include, but are not limited to, the inside region of the knees, the middle to upper area of the upper arm, including the tricep area, the submental area, including the area under the chin, for example the wattle (which is understood to refer to the fleshy fold of skin in the submental area of a patient), the abdomen, the hips, the inner thigh, the outer thigh, the buttocks, an upper arms region of the patient, the lower back, upper back and the chest.

In certain embodiments, provided are pharmaceutical and/or cosmetic formulations and methods of treatment comprising the pharmaceutical and/or cosmetic formulations that are formulated to provide a sub-dose of salmeterol xinafoate between about 20 μg and about 1 ng, between about 20 μg and about 2 ng, between about 20 μg and about 3 ng, between about 20 μg and about 4 ng, between about 20 μg and about 5 ng, between about 20 μg and about 6 ng, between about 20 μg and about 7 ng, between about 15 μg and about 8 ng, between about 10 μg and about 9 ng, between about 5 μg and about 10 ng, between about 1 μg and about 12 ng, between about 900 ng and about 14 ng, between about 800 ng and about 16 ng, between about 700 ng and about 18 ng, between about 600 ng and about 20 ng, between about 550 ng and about 22 ng, between about 500 ng and about 24 ng, between about 450 ng and about 26 ng, between about 400 ng and about 28 ng, between about 350 ng and about 30 ng, between about 300 ng and about 32 ng, between about 250 ng and about 34 ng, between about 200 ng and about 36 ng, between about 150 ng and about 38 ng, between about 125 ng and about 40 ng, between about 100 ng and about 42 ng, between about 90 ng and about 44 ng, between about 80 ng and about 46 ng, between about 75 ng and about 48 ng, between about 70 ng and about 50 ng, between about 69 ng and about 51 ng, between about 68 ng and about 52 ng, between about 67 ng and about 53 ng, between about 66 ng and about 54 ng, between about 65 ng and about 55 ng, between about 64 ng and about 56 ng, between about 63 ng and about 57 ng, between about 62 ng and about 58 ng, between about 61 ng and about 59 ng, or about 60 ng.

In some embodiments, provided herein are pharmaceutical and/or cosmetic formulations, and methods of treatment comprising administration of the pharmaceutical and/or cosmetic formulations, that are formulated to provide a sub-dose of salmeterol xinafoate that is equal to or less than about 20 μg, equal to or less than about 19 μg, equal to or less than about 18 μg, equal to or less than about 17 μg, equal to or less than about 16 μg, equal to or less than about 15 μg, equal to or less than about 14 μg, equal to or less than about 13 μg, equal to or less than about 12 μg, equal to or less than about 11 μg, equal to or less than about 10 μg, equal to or less than about 9 μg, equal to or less than about 8 μg, equal to or less than about 7 μg, equal to or less than about 6 μg, equal to or less than about 5 μg, equal to or less than about 4 μg, equal to or less than about 3 μg, equal to or less than about 2 μg, equal to or less than about 1 μg, equal to or less than about 975 ng, equal to or less than about 950 ng, equal to or less than about 925 ng, equal to or less than about 900 ng, equal to or less than about 875 ng, equal to or less than about 850 ng, equal to or less than about 825 ng, equal to or less than about 800 ng, equal to or less than about 775 ng, equal to or less than about 750 ng, equal to or less than about 725 ng, equal to or less than about 700 ng, equal to or less than about 675 ng, equal to or less than about 650 ng, equal to or less than about 625 ng, equal to or less than about 600 ng, equal to or less than about 575 ng, equal to or less than about 550 ng, equal to or less than about 525 ng, equal to or less than about 500 ng, equal to or less than about 475 ng, equal to or less than about 450 ng, equal to or less than about 425 ng, equal to or less than about 400 ng, equal to or less than about 375 ng, equal to or less than about 350 ng, equal to or less than about 325 ng, equal to or less than about 300 ng, equal to or less than about 275 ng equal to or less than about 250 ng, equal to or less than about 225 ng, equal to or less than about 200 ng, equal to or less than about 175 ng, equal to or less than about 150 ng, equal to or less than about 125 ng, equal to or less than about 100 ng, equal to or less than about 75 ng, or equal to or less than about 50 ng, or equal to or less than about 25 ng, equal to or less than about 20 ng, equal to or less than about 15 ng, equal to or less than about 10 ng, equal to or less than about 5 ng, or equal to or less than about 1 ng.

Suitable tissue concentrations of salmeterol via subcutaneous administration for adipose tissue treatment include from about 1 pM to about 100 μM, e.g., about 0.01 μM to about 50 μM, 0.5 μM to about 50 μM, about 2.0 μM to about 50 μM, about 5 μM to about 50 μM, about 10 μM to about 50 μM, about 20 μM to about 75 μM, or any other tissue concentration of salmeterol from about 0.1 nM to about 100 μM.

Pharmacokinetic Parameters

In another aspect is a pharmaceutical and/or cosmetic formulation, including certain methods of treatment comprising administration of the pharmaceutical and/or cosmetic formulations described herein, comprising an adipose tissue-reducing amount of salmeterol or a salt, optical isomer, racemate, solvate, or polymorph thereof and at least one subcutaneously acceptable inactive ingredient, wherein the formulation provides a mean plasma salmeterol $C_{max}$ equal to or less than about 300 pg/mL when administered subcutaneously. In one embodiment, the formulation provides a mean plasma salmeterol $C_{max}$ equal to or less than about 270 pg/mL. In one embodiment, the formulation provides a mean plasma salmeterol $C_{max}$ equal to or less than about 250, about 230, about 200, about 190, about 180, about 170, about 160, about 150, about 140, about 130, about 120, about 110, about 100, about 90, about 80, about 70, about 60, about 50, about 40, about 30, about 20, about 10, about 3, about 1 pg/mL, or is undetectable using conventional methodology. For purposes of this application, "undetectable using conventional methodology" or "undetectable using current methodology," means that the concentration is lower than the low limit of quantitation (LLOQ) using the Liquid Chromatography/Mass Spectrometry/Mass Spectrometry (LC/MS/MS) method, which is understood in the art to be a type of tandem mass spectrometry for determining $C_{max}$ levels. In still further or additional embodiments, the formulations described herein provide a mean plasma salmeterol $C_{max}$ that is between undetectable levels and about 300 pg/mL, about 1 pg/mL to about 270 pg/mL, about 5 pg/mL to about 250 pg/mL, about 10 pg/mL to about 220 pg/mL, about 15 pg/mL to about 200 pg/mL, about 25 pg/mL to about 170 pg/mL, about 50 pg/mL to about 150 pg/mL, or about 75 pg/mL to about 100 pg/mL.

Partitioning Into Adipose Tissue

In a further aspect is a pharmaceutical and/or cosmetic formulation comprising an adipose tissue-reducing amount of salmeterol or a salt, optical isomer, racemate, solvate, or polymorph thereof and at least one subcutaneously acceptable inactive ingredient, wherein the formulation provides a salmeterol plasma $C_{max}$ ratio of subcutaneous to intravenous administration of between about 0.01 to about 0.4 when administered subcutaneously (also known as the "salmeterol partition" ratio) For purposes of this application, the ratio of plasma $C_{max}$ of a long-acting beta-2 adrenergic receptor agonist administered subcutaneously to the plasma $C_{max}$ of the same long-acting beta-2 adrenergic receptor agonist administered intravenously is known as the "partition" ratio. Thus, in one embodiment, the partition ratio of salmeterol is about 0.01 to about 0.4. In another embodiment, the salmeterol partition ratio is about 0.05 to about 0.3. In another embodiment, the salmeterol partition ratio is from about 0.1 to about 0.35. In a further embodiment, the salmeterol partition ratio is about 0.1. In another embodiment, the salmeterol partition ratio is between 0.05 to about 0.2. In a further embodiment, the salmeterol partition ratio is between about 0.1 to about 0.2. In yet another embodiment, the salmeterol partition ratio is about 0.01, about 0.02, about 0.03, about 0.04, about 0.05, about 0.06, about 0.07, about 0.08, about 0.09, about 0.1, about 0.11, about 0.12, about 0.13, about 0.14, about 0.015, about 0.16, about 0.17, about 0.18, about 0.19, about 0.2, about 0.21, about 0.22, about 0.23, about 0.24, about 0.25, about 0.26, about 0.27, about 0.28, about 0.29, about 0.30, about 0.31, about 0.32, about 0.33, about 0.34, about 0.35, about 0.36, about 0.37, about 0.38, about 0.39, about 0.40. By way of a non-limiting example only, salmeterol xinafoate formulated in 5% PEG-400 in 0.9% saline USP, at various concentrations were administered to non-naive Gottingen minipigs via single intravenous injection or subcutaneous injection. The salmeterol partition ratio was calculated as the average salmeterol plasma $C_{max}$ of subcutaneous administration ((403+575)/2) divided by the average salmeterol plasma $C_{max}$ of intravenous administration ((4950+4290)/2). Thus, in this non-limiting example, the salmeterol partition ratio was determined to be 0.1. In a further embodiment, is a subcutaneous formulation comprising of salmeterol or a salmeterol-like compound and a subcutaneously acceptable excipient wherein the formulation provides a partition ratio of between about 0.01 and about 0.4. As used herein, a salmeterol-like compound is a compound having a partition ratio of between about 0.01 and 0.4 and provides limited systemic exposure, and consequently, a reduced or minimized risk of producing cardiovascular side effects. Additionally, salmeterol-like compounds also selectively partition into the adipose tissue due to their lipophilic nature. In another embodiment, provided is a pharmaceutical and/or cosmetic formulation providing a salmeterol partition ratio of between about 0.01 to about 0.2. In one embodiment, the formulation provides a salmeterol partition ratio of between about 0.01 to about 0.3. In yet a further embodiment, the formulation provides a salmeterol partition ratio of between about 0.01, about 0.02, about 0.03, about 0.04, about 0.05, about 0.06, about 0.07, about 0.08, about 0.09, about 0.1, about 0.11, about 0.12, about 0.13, about 0.14, about 0.015, about 0.16, about 0.17, about 0.18, about 0.19, about 0.2.

In some embodiments, provided herein is a formulation that is formulated to provide a single session dose of salmeterol xinafoate in an amount that is about 5 ng to about 20 μg and that provides a salmeterol plasma $C_{max}$ ratio of subcutaneous to intravenous administration of between about 0.01 to about 0.4 when administered subcutaneously. In some embodiments, provided herein are pharmaceutical and/or cosmetic formulations comprising a weekly dose of salmeterol xinafoate that is between about 5 ng to about 150 μg. In a particular embodiment, provided herein are pharmaceutical and/or cosmetic formulations comprising a weekly dose of salmeterol xinafoate that is less than about 5 μg. In still further embodiments, provided herein is a pharmaceutical and/or cosmetic formulation comprising a sub-dose of salmeterol xinafoate in an amount that is between about 1 ng to about 50 μg In a further aspect is a subcutaneous formulation consisting essentially of a long-acting beta-2 receptor agonist and a subcutaneously acceptable excipient thereof, wherein the formulation provides a partition ratio lower than the partition ratio of a reference long-acting beta-2 receptor agonist. In one embodiment, the subcutaneous formulation provides a partition ratio of about four to six times lower than the partition ratio of a reference long-acting beta-2 receptor agonist. In one embodiment, the formulation described herein provides a partition ratio about five times lower than the partition ratio of a reference long-acting beta-2 receptor agonist. In another embodiment, the reference long-acting beta-2 receptor agonist is lipophilic. In yet another embodiment, the reference long-acting beta-2 receptor agonist is formoterol.

In yet a further embodiment, the salmeterol formulation provides a partition ratio about five times lower than a reference long-acting beta-2 receptor agonist, wherein the reference long-acting beta-2 adrenergic receptor agonist is formoterol.

Methods

Another feature of the subject matter provided herein are pharmaceutical methods and cosmetic methods utilizing the formulations provided herein. In some embodiments, provided herein is a cosmetic method for reducing adiposity in a human patient comprising subcutaneously administering a pharmaceutical or cosmetic formulation that is suitable for subcutaneous injection consisting essentially of: (a) active ingredient that consists essentially of a cosmetically effective adipose tissue-reducing amount of one or more lipophilic long-acting selective beta-2 adrenergic receptor agonists, or salts, solvates, or polymorphs thereof; and (b) one or more subcutaneously acceptable inactive ingredients. In another embodiment, provided herein is a cosmetic method for reducing adiposity in a human patient comprising subcutaneously administering a pharmaceutical formulation suitable for subcutaneous injection consisting of (a) active ingredient that consists essentially of a cosmetically effective adipose tissue-reducing amount of one or more lipophilic long-acting selective beta-2 adrenergic receptor agonists, or salts, solvates, or polymorphs thereof; and (b) one or more subcutaneously acceptable inactive ingredients. In still further embodiments, provided herein is a cosmetic method for reducing adiposity in a human patient comprising subcutaneously administering a pharmaceutical formulation suitable for subcutaneous injection comprising: (a) active ingredient that consists essentially of a cosmetically effective adipose tissue-reducing amount of one or more lipophilic long-acting selective beta-2 adrenergic receptor agonists, or salts, solvates, or polymorphs thereof; and (b) one or more subcutaneously acceptable inactive ingredients. In still further embodiments, provided herein is a cosmetic method for inducing lipolysis in adipose tissue of a human patient comprising subcutaneously administering a pharmaceutical formulation suitable for subcutaneous injection consisting essentially of: (a) active ingredient that consists essentially of a cosmetically effective adipose tissue-reducing amount of one or more lipophilic long-acting selective beta-2 adrenergic receptor agonists, or salts, solvates, or polymorphs thereof; and (b) one or more subcutaneously acceptable inactive ingredients. In specific embodiments of the methods and formulations described herein, the injectable formulations are substantially free of glucocorticosteroids.

Methods of Reducing Adipose Tissue

In another aspect, provided herein are methods for reducing adipose tissue in a patient comprising administering to the patient a pharmaceutical and/or cosmetic formulation comprising a lipophilic long-acting selective beta-2 adrenergic receptor agonist (as single agent therapy) and at least one subcutaneously acceptable inactive ingredient. In one aspect is a method for reducing adipose tissue in a subject comprising subcutaneously administering to the subject a pharmaceutical and/or cosmetic formulation comprising an active agent consisting essentially of an adipose tissue-reducing amount of a lipophilic long-acting selective beta-2 adrenergic receptor agonist or a salt, optical isomer, racemate, solvate, or polymorph thereof and at least one subcutaneously acceptable inactive ingredient wherein adipose tissue in the subject is reduced. In one embodiment, the lipophilic long-acting selective beta-2 adrenergic receptor agonist is salmeterol. In yet another embodiment, the salt of the lipophilic long-acting selective beta-2 adrenergic agonist is a xinafoate salt.

In yet a further embodiment, the subcutaneous administration results in a reduced or minimized risk of producing an increase in heart rate or a decrease in blood pressure or a combination thereof. In another embodiment, the subcutaneous administration provides a minimized risk of producing anaphylaxis related effects, such as, flushing, reddening, rapid heart rate, chest tightness, difficulty breathing, faintness, heart palpitations, hives, atrophy, pigmentation, nodularity, necrosis, irregular or abnormal heart rate, paroxysmal bronchoconstriction, and hypersensitivity reaction such as angioedema and urticaria. By way of a non-limiting example only, a subcutaneous formulation comprising salmeterol was administered to Gottingen minipigs. The salmeterol partition ratio is determined as described above. Thus, in this non-limiting example, the subcutaneous formulation administered to minipigs provides a salmeterol partition ratio of 0.1 and a reduced or minimized risk of producing cardiovascular side effects. It should be noted that the reduced or minimized risk described herein (due to limited systemic exposure) refers to a generalized population and may vary depending on the individual subject or patient. Subcutaneous formulations consisting essentially of salmeterol provide therapeutic effect to a regional fat deposit and a reduced or minimized risk of producing the side effects associated with the use of other long-acting beta-2 agonists or long-acting beta-2 agonists administered by other methods. Such side effects include paradoxical bronchospasm, high blood pressure, abnormal heart rhythm, abnormally low blood pressure, an increase in asthma related conditions, bronchospasm, inflammation of the lining of the stomach and intestines, involuntary quivering, fast heartbeat, chest pain, and giant hives.

Methods of Treating Regional Fat Accumulation

In yet another aspect, provided herein are methods for treating regional fat accumulation in a patient comprising administering to the patient a pharmaceutical and/or cosmetic formulation comprising a lipophilic long-acting selective beta-2 adrenergic receptor agonist (as single agent therapy) and at least one subcutaneously acceptable inactive ingredient. In further embodiments, the method for treating regional fat accumulation in a subject comprises subcutaneously administering to a regional fat accumulation area a pharmaceutical and/or cosmetic formulation comprising a regional fat accumulation reducing amount of salmeterol or a salt, optical isomer, racemate, solvate, or polymorph thereof and at least one subcutaneously acceptable inactive ingredient. In further or additional embodiments, the formulation provides a mean plasma salmeterol $C_{max}$ equal that is in the range of about 300 pg/mL to levels that are undetectable using conventional methodology, wherein the regional fat accumulation in the subject is reduced. In one embodiment, salmeterol selectively partitions into adipose tissue of the regional fat accumulation relative to plasma.

Also described herein is a method for treating regional fat accumulation comprising subcutaneously administering to the subject a pharmaceutical and/or cosmetic formulation comprising an active agent consisting essentially of a regional fat accumulation reducing amount of a long-acting selective beta-2 adrenergic receptor agonist or a salt, optical isomer, racemate, solvate, or polymorph thereof and at least one subcutaneously acceptable inactive ingredient. In one embodiment, the lipophilic long-acting selective beta-2 adrenergic receptor agonist is salmeterol. In another embodiment, the salt of the lipophilic long-acting selective beta-2 adrenergic agonist is a xinafoate salt. In a further embodiment, the subcutaneous administration reduces or minimizes the risk of producing cardiovascular side effects (by minimizing systemic exposure).

Methods of Inducing Lipolysis in Adipose Tissue

As discussed herein, lipolysis and/or inhibition of adipogenesis are stimulated by the beta-1, 2, or 3 receptor subtypes. Thus, agonists to one, two and/or all three receptors are capable of stimulating lipolysis and/or inhibition of adipogenesis. In humans, beta-2 receptor activity is believed to be more important for stimulating lipolysis. Lipolytic activity and adipocyte proliferation inhibition are believed to be mediated through modulation of adrenergic receptors in adipose tissue and/or on adipocytes.

In another aspect, provided herein is a method for inducing lipolysis in adipose tissue comprising subcutaneously administering a pharmaceutical and/or cosmetic formulation suitable for subcutaneous injection comprising:(a) a lipophilic long-acting selective beta-2 adrenergic receptor agonist; and (b) at least one subcutaneously acceptable inactive ingredient. In one aspect is a method for inducing lipolysis in a subject comprising subcutaneously administering to the subject a pharmaceutical and/or cosmetic formulation comprising an active agent consisting essentially of an adipose tissue-reducing amount of a lipophilic long-acting selective beta-2 adrenergic receptor agonist or a salt, optical isomer, racemate, solvate, or polymorph thereof and at least one subcutaneously acceptable inactive ingredient that induced lipolysis in a patient, and reduces adipose tissue in the area treated. In one embodiment, the lipophilic long-acting selective beta-2 adrenergic receptor agonist is salmeterol. In yet another embodiment, the salt of the lipophilic long-acting selective beta-2 adrenergic agonist is a xinafoate salt.

Methods of Aesthetic Treatment of Contour Defects Such as Bulging

In an aspect, provided herein is a method for the aesthetic treatment of body contour defects or deformities in a human patient comprising subcutaneous or transcutaneous administration of a formulation comprising an adipose tissue-reducing amount of one or more beta-2 adrenergic receptor agonists, or salts, solvates, or polymorphs thereof. In certain embodiments, the body contour defect treated is an abdominal contour defect. In certain embodiments, the body contour defect treated comprises abdominal bulging. In some embodiments, the body contour defect treated is a gluteal contour defect. In an embodiment, the body contour defect treated is bulging in an area which is one or more of the neck, upper arms, female and male breasts, abdomen, flanks, back, hips, buttocks, thighs, knees and ankles. In certain embodiments, the individual being treated has a history of prior treatment of contour defects (e.g., abdominoplasty, liposuction, or exposure to ablative or body contouring devices, mesotherapy or lipolytic agents).

In some embodiments, the beta-2 adrenergic receptor agonist administered for treatment of contour defects, is selective for the beta-2 adrenergic receptor. In further or additional embodiments, the beta-2 adrenergic receptor agonist is lipophilic. In further or additional embodiments, the beta-2 adrenergic receptor agonist is long-acting. In an embodiment, the lipophilic long-acting selective beta-2 adrenergic receptor agonist is salmeterol. In a further embodiment, the polymorph is polymorph I or II. In further embodiments, the formulation uses a mixture of salmeterol polymorphs. In yet another embodiment, the salt of the lipophilic long-acting selective beta-2 adrenergic receptor agonist is a xinafoate salt. In some embodiments, the lipophilic long-acting selective beta-2 adrenergic receptor agonist is salmeterol xinafoate.

In a further aspect, provided herein is a method for the aesthetic treatment of body contour defects such as bulging in a human patient comprising subcutaneously administering a formulation suitable for subcutaneous injection comprising: (a) active ingredient that consists essentially of a cosmetically effective adipose tissue-reducing amount of one or more lipophilic long-acting selective beta-2 adrenergic receptor agonists, or salts, solvates, or polymorphs thereof; and (b) one or more subcutaneously acceptable inactive ingredients. In certain embodiments, the body contour defect treated is abdominal bulging. In some embodiments, the body contour defect treated is a gluteal contour defect comprising bulging. In one embodiment, the lipophilic long-acting selective beta-2 adrenergic receptor agonist is salmeterol. In yet another embodiment, the salt of the lipophilic long-acting selective beta-2 adrenergic agonist is a xinafoate salt. In a further embodiment, the subcutaneous administration reduces or minimizes the risk of producing cardiovascular side effects (by minimizing systemic exposure). In an embodiment, the, formulation provides a mean plasma salmeterol $C_{max}$ equal that is in the range of about 300 pg/mL to levels that are undetectable using conventional methodology, wherein the body contour defect in the subject is treated.

In an aspect provided is a method for aesthetic treatment of cheek contour defect in a human patient by contacting a targeted fat deposit in the cheek with a composition comprising an adipose tissue-reducing amount of one or more beta-2 adrenergic receptor agonists, or salts, solvates, or polymorphs thereof. In certain embodiments, the fat deposit targeted is buccal fat. In some embodiments, the fat deposit is subcutaneous cheek fat. In certain embodiments, the patient suffers from chipmunk cheeks. In some embodiments, the beta-2 adrenergic receptor agonist administered is selective for the beta-2 adrenergic receptor. In further or additional embodiments, the beta-2 adrenergic receptor agonist is lipophilic. In further or additional embodiments, the beta-2 adrenergic receptor agonist is long-acting. In an embodiment, the lipophilic long-acting selective beta-2 adrenergic receptor agonist is salmeterol. In a further embodiment, the polymorph is polymorph I or II. In further embodiments, the formulation uses a mixture of salmeterol polymorphs. In yet another embodiment, the salt of the lipophilic long-acting selective beta-2 adrenergic receptor agonist is a xinafoate salt. In some embodiments, the lipophilic long-acting selective beta-2 adrenergic receptor agonist is salmeterol xinafoate.

In a further aspect provided is a method for aesthetic treatment of cheek contour defect in a human patient by contacting a targeted fat deposit in the cheek with a composition comprising: (a) active ingredient that consists essentially of a cosmetically effective adipose tissue-reducing amount of one or more lipophilic long-acting selective beta-2 adrenergic receptor agonists, or salts, solvates, or polymorphs thereof; and (b) one or more subcutaneously acceptable inactive ingredients. In an embodiment is a method for aesthetic treatment of cheek contour defect in a human patient by contacting a targeted fat deposit in the cheek with a composition essentially comprising: (a) active ingredient that consists essentially of a cosmetically effective adipose tissue-reducing amount of one or more lipophilic long-acting selective beta-2 adrenergic receptor agonists, or salts, solvates, or polymorphs thereof; and (b) one or more subcutaneously acceptable inactive ingredients. In a further embodiment is a method for aesthetic treatment of cheek contour defect in a human patient by contacting a targeted fat deposit in the cheek with a composition consisting of: (a) active ingredient that consists essentially of a cosmetically effective adipose tissue-reducing amount of one or more lipophilic long-acting selective beta-2 adrenergic receptor agonists, or salts, solvates, or polymorphs thereof; and (b) one or more subcutaneously acceptable inactive ingredients. In some embodiments, the patient suffers from chipmunk cheeks. In certain embodiments, the fat deposit targeted is buccal fat. In some embodiments, the fat deposit is subcutaneous cheek fat. In one embodiment, the lipophilic long-acting selective beta-2 adrenergic receptor agonist is salmeterol. In yet another embodiment, the salt of the lipophilic long-acting selective beta-2 adrenergic agonist is a xinafoate salt. In a further embodiment, the subcutaneous administration reduces or minimizes the risk of producing cardiovascular side effects (by minimizing systemic exposure). In an embodiment, the, formulation provides a mean plasma salmeterol $C_{max}$ equal that is in the range of about 300 pg/mL to levels that are undetectable using conventional methodology, wherein the body contour defect in the subject is treated.

Methods of Treatment of Thyroid Eye Disease

In an aspect provided herein are compositions, formulations, methods, and systems for treating thyroid eye disease by contacting a targeted fat deposit in the eye with a composition, said composition comprising: one or more beta-2 adrenergic receptor agonists, or salts, solvates, or polymorphs thereof. In some embodiments is provided a method of treating proptosis by subcutaneous administration of a composition comprising one or more lipophilic long-acting selective beta-2 adrenergic receptor agonists, or salts, solvates, or polymorphs thereof.

In some embodiments, the beta-2 adrenergic receptor agonist administered is selective for the beta-2 adrenergic receptor. In further or additional embodiments, the beta-2 adrenergic receptor agonist is lipophilic. In further or additional embodiments, the beta-2 adrenergic receptor agonist is long-acting. In an embodiment, the lipophilic long-acting selective beta-2 adrenergic receptor agonist is salmeterol. In a further embodiment, the polymorph is polymorph I or II. In further embodiments, the formulation uses a mixture of salmeterol polymorphs. In yet another embodiment, the salt of the lipophilic long-acting selective beta-2 adrenergic receptor agonist is a xinafoate salt. In some embodiments, the lipophilic long-acting selective beta-2 adrenergic receptor agonist is salmeterol xinafoate.

In a further aspect, provided herein is a method for treating thyroid eye disease by contacting a targeted fat deposit in the eye with a composition comprising: (a) active ingredient that consists essentially of an adipose tissue-reducing amount of one or more lipophilic long-acting selective beta-2 adrenergic receptor agonists, or salts, solvates, or polymorphs thereof; and (b) one or more subcutaneously acceptable inactive ingredients. In some embodiments is provided a method of treating proptosis by subcutaneous administration of a composition comprising: (a) active ingredient that consists essentially of an adipose tissue-reducing amount of one or more lipophilic long-acting selective beta-2 adrenergic receptor agonists, or salts, solvates, or polymorphs thereof; and (b) one or more subcutaneously acceptable inactive ingredients. In some embodiments, the lipophilic long-acting selective beta-2 adrenergic receptor agonist is salmeterol xinafoate.

Pharmaceutically and Cosmetically Acceptable Excipients

In some embodiments, the pharmaceutical and/or cosmetic formulations provided herein comprise a selective, lipophilic, long-acting beta-2 adrenergic agonist that is soluble at the desired concentration and therefore no co-solvent is needed to formulate an injectable solution.

In a further embodiment, the formulations provided herein comprise at least one co-solvent is selected from about 0.25 to about 40% polyethylene glycol, or from about 0.5 to about 20% polyethylene glycol, or from about 0.75 to about 10% polyethylene glycol, or from about 1 to about 5% polyethylene glycol, or from about 2 to about 4% polyethylene glycol. In further or additional embodiments, the polyethylene glycol is about 0.8—about 1%, or is about 0.9% polyethylene glycol. In a further embodiment, the polyethylene glycol is PEG 400.

In yet a further embodiment, the formulations described herein comprise at least one subcutaneously acceptable excipient that is selected from about 0.01 to about 10% polysorbate, about 0.05 to about 5% polysorbate, about 0.1 to about 2% polysorbate, or about 0.5 to about 1% polysorbate. In some embodiments, the polysorbate is about 0.01—about 2% polysorbate. In still further embodiments, the polysorbate is about 0.04%. In one embodiment, the polysorbate is polysorbate 80.

Excipients used in the formulations described herein include, but are not limited to, suspending agents, surfactants, solubilizers such as, for example, PEG 400, stabilizers, diluents and the like, and should be selected on the basis of compatibility with the lipophilic long-acting beta-2 adrenergic receptor agonist. In some embodiments, a polyalkylene glycol or a mixture of different polyalkylene glycols is used as a solubilizer. Polyalkylene glycols from the group of polypropylene glycols or polyethylene glycols are particularly suitable in this connection because of the physiological tolerance. In this connection, the use of polyethylene glycols is utilized in some embodiments presented herein. In some embodiments, polyethylene glycols such as, for example, PEG 400, is contemplated herein.

Additives increasing the bioavailability of a lipophilic long-acting beta-2 adrenergic receptor agonist, such as, salmeterol are, in some embodiments, organic compounds, salts thereof, optical isomers or racemates thereof, emulsions or dispersions containing organic compounds or salts thereof, e.g. dispersions of polar lipids, or any combination. Organic compounds useful in the subcutaneous formulation are e.g. amino acids, peptides, proteins, and polysaccharides. Peptides include dipeptides, tripeptides, oligopeptides, such as collagen and gelatin. In some embodiments, the collagen and gelatin is hydrolyzed. Polysaccharides include e.g., chitosans, cyclodextrins, starch, hyaluronic acids, dextrans, cellulose, and any derivatives, combinations. In further embodiments, the starch is hydrolyzed. The emulsions include oil-in-water emulsions with oil as the dispersed phase and water-in-oil dispersions with oil as the continuous phase. In other embodiments, the oil is of vegetable or of animal origin or synthetically produced. In further embodiments, the polar liquids are one or more phospholipids or glycolipids or any combination thereof. In some other embodiments, the additives increasing the bioavailability of a lipophilic long-acting beta-2 adrenergic receptor agonist, such as, salmeterol are added to a stable solution or dispersion containing the lipophilic long-acting beta-2 adrenergic receptor agonist.

In further embodiments, before administration, one or more aqueous solutions or dispersions are added, in any mixture or sequence, to the lipophilic long-acting beta-2 adrenergic receptor agonist, such as, salmeterol, which is a stable aqueous solution. In other embodiments, the formulation is a stable aqueous solution ready for administration. In some embodiments, it is a dispersion, e.g. a suspension, a liposomal formulation or an emulsion. In yet other embodiments, the formulation also comprises a salt in order to give an isotonic solution, e.g., NaCl, KCl, and/or in further embodiments, it comprises one or more other isotonicity establishing compounds.

In yet other embodiments, an amino acid is used to buffer the system. In some embodiments, a suitable buffer is glycine, lysine, arginine, histidine or glycylglycine, in other embodiments, the buffer is glycylglycine.

In some other embodiments, a non-ionic surfactant is also present in the formulation. In some embodiments, the surfactant is chosen from block-copolymers, such as a poloxamer, e.g., poloxamer 188, or a polyoxyethylene sorbitan fatty acid ester, such as polyoxyethylene-(20)-sorbitan monolaurate or polyoxyethylene-(20)-sorbitan monooleate. Also disclosed herein are formulations using polyoxyethylene-(20)-sorbitan monolaurate (Tween 20). In one embodiment, the formulation described herein used polyoxyethylene-(20)-sorbitan monooleate (Tween 80). In other embodiments, the non-ionic surfactant, is present in an amount above the critical micelle concentration (CMC).

Also presented herein are mono- or disaccharides (e.g., sucrose), polysaccharides such as low molecular weight dextrins, or sugar alcohols (e.g., sorbitol, glycerol or mannitol) used in the subcutaneous formulations. In some embodiments, the formulation also comprises antioxidants such as bisulfite, ascorbate glutathione, acetylcystein, tocopherol, methionin, EDTA, citric acid, butyl hydroxy toluene and/or butyl hydroxy anisole. In other embodiments, complexing agents, such as EDTA and citric acid are also present in small concentrations for stabilizing the lipophilic long-acting beta-2 adrenergic receptor agonist, such as, salmeterol. Furthermore, in other embodiments, preservatives such as benzyl alcohol, phenol, sorbic acid, parabens, and chlorocresol are added. In further or additional embodiments, the lipophilic selective long-acting beta-2 adrenergic receptor agonist, such as, salmeterol or formoterol, is prepared as a lyophile. In further or additional embodiments, a lyophilized lipophilic selective long-acting beta-2 adrenergic receptor agonist is prepared such that it can be reconstituted for administration via subcutaneous injection to a patient.

Routes of Administration

Injectable formulations are administered using any method known in the art, for example, using a single needle, multiple needles, and/or using a needleless injection device. In some embodiments, a tissue loading dose of the active ingredients formulated in a suitable carrier delivered by injection. In some embodiments, delivery comprises single needle injection. In some embodiments, delivery comprises injection using a multi-needle array, which, in some embodiments, provides a wide dispersion of the formulation in the target tissue. In some embodiments, formulations are injected in a manner that allows dispersal into the appropriate layer of subcutaneous fat in or near regional fat areas.

Transcutaneous formulations, also contemplated as a route of delivery for the pharmaceutical and/or cosmetic formulations and methods of treatment provided herein, are administered using any known method in the art.

Embodiments of the composition are formulated for administered by any suitable method, for example, as described in *Remington: The Science And Practice Of Pharmacy* (21st ed., Lippincott Williams & Wilkins) Exemplary routes of administration include, but are not limited to parenteral, subcutaneous, or intramuscular. In some embodiments, the composition is formulated for injection of an area at which treatment is desired, for example, in or near a regional fat deposit.

Any suitable pharmaceutically and/or cosmetically acceptable excipient appropriate for a particular route of administration can be used. Examples of pharmaceutically and/or cosmetically acceptable carriers include, but are not limited to, buffers, saline, or other aqueous media. The compounds described herein are in some embodiments, soluble in the carrier which is employed for their administration (e.g., subcutaneous). Some embodiments comprise any suitable lipophilic carrier, for example, modified oils (e.g., Cremophor® BASF, Germany), soybean oil, propylene glycol, polyethylene glycol, derivatized polyethers, combinations thereof, and the like. Some embodiments comprise one or more carriers or agents, suitable for subcutaneous administration. Some embodiments comprise excipients suitable for stable suspensions for beta-2 receptor agonists. In some embodiments, the pharmaceutical and/or cosmetic formulations comprise polyethylene glycol in an amount of from about 0.5% to about 40%. In another embodiment, the formulation suitable for subcutaneous administration comprises polyethylene glycol in an amount from about 0.5% to 40%, about 1% to about 35%, about 2% to about 30%, about 3% to about 25%, about 4% to about 20%, about 5% to about 15%, about 10% to about 12%, or is about 1%, about 2%, about 3%, about 4%, about 5%, about 10%, about 15%, about 20%, about 25%, about 30%, about 35%, or about 40%. In a further embodiment, polyethylene glycol is in an amount of about 20%. In yet a further embodiment, polyethylene glycol is PEG 400. In yet another embodiment, the pharmaceutical and/or cosmetic formulations comprise polysorbate in an amount of from 0.01% to about 10%. In another embodiment, the formulation suitable for subcutaneous administration comprises polysorbate in an amount from about 0.01% to about 10%, about 0.02% to about 9%, about 0.03% to about 8%, about 0.04% to about 7%, about 0.05% to about 6%, about 0.06% to about 5%, about 0.07% to about 4%, about 0.08% to about 3%, about 0.09% to about 2%, 0.1% to about 1%, about 0.2% to about 0.5%, or is about 0.01%, about 0.02%, about 0.03%, about 0.04%, about 0.05%, about 0.1%, about 0.2%, about 0.3%, about 0.4%, about 0.5%, about, about 0.6%, about 0.7%, about 0.8%, about 0.9%, about 1%, about 2%, about 3%, about 4%, about 5%, about 6%, about 7%, about 8%, and about 9%. In a further embodiment, polysorbate is in an amount of about 10%. In yet a further embodiment, polysorbate is polysorbate 80. In further or additional embodiments, the lipophilic, selective long-acting beta-2 adrenergic receptor agonist, such as, salmeterol or formoterol, is prepared as a lyophile. In further or additional embodiments, a lyophilized lipophilic, selective long-acting beta-2 adrenergic receptor agonist is reconstituted for administration via subcutaneous injection to a patient.

In other embodiments, another delivery mode comprises a needless pressurized injection device. In some embodiments, of these devices, the formulation is pressurized mechanically or pneumatically, for example, using a gas such as helium or carbon dioxide, and then forced through a small orifice into the body tissues, thereby delivering the formulation subcutaneously. Suitable formulations for needless injections are known, for example, liquid, solutions, suspensions, gels, colloids, emulsions, and dry powders. An advantage of this system is a wide dispersal area compared with typical needle injection systems. Needless injection under the appropriate pressure forces the formulation into a more planar delivery pattern, with fingers of formulation spreading out radially following paths of least resistance. In contrast, delivery by a typical needle injection results in a globular delivery of the formulation. Needless injection also permits precise control of the depth of penetration by controlling the injection pressure and orifice size. Thus, needless injection is a delivery method for a sub-dermal injection contemplated herein of a formulation for treating superficial fat accumulations, which is useful, for example, for smoothing skin dimpling caused by fat. In other embodiments, needless injection is also used for deeper fat accumulations. In further embodiments, a needless device also provides easy and convenient multiple injections of the formulation over a defined region with a large lateral spread.

Treatment of Other Conditions

In some embodiments, the formulations described herein are used for treating immune and inflammation-related dermal conditions including psoriasis, atopic dermatitis, vitiligo, hypopigmentation, stria, and wrinkles or rhytids. In one embodiment, a lipophilic, selective long-acting selective beta-2 agonists is administered subcutaneously to treat a condition of a human patient. In another embodiment, a beta agonist is used for treating immune and inflammation-related dermal conditions. In some embodiments, subcutaneously administrable lipophilic, selective long-acting beta-adrenergic agonist treatment is used to decrease Langerhans cell migration and antigen presentation.

In some embodiments, beta-2 adrenergic receptor agonists are administered subcutaneously for the treatment of skin wrinkles and skin stria, or stretch marks. Cutaneous stria is characterized by a thinning of the dermis, with a loss of collagen and hypopigmentation. Long-acting beta-adrenergic agonists promote the recruitment and proliferation and collagen production of dermal fibroblasts in the stria. In addition, they stimulate melanocytes to repigment the stria. Thus, in some embodiments a subcutaneous formulation consisting essentially of an adipose tissue-reducing amount of salmeterol or a salt, solvate, or polymorph thereof is used to treat these conditions.

In some embodiments, beta-2 adrenergic receptor agonists are administered to increase skeletal muscle mass and cause hypertrophy and increased protein synthesis, effects which are mediated through intracellular in increases cAMP levels. Similar to adipocytes, exposure to beta-2 adrenergic receptor agonists results in receptor down-regulation. Thus, the disclosed formulations are also used for treating skeletal muscle injury or conditions where increasing skeletal muscle mass is important. In some embodiments, the methods described herein are used to increase facial muscle tone and provide a more youthful appearance. In some embodiments, the methods described herein are used to treat strabismus or lazy eye by strengthening ocular muscles.

In other embodiments, provided are methods for decreasing cellulite in a subject, also known as adiposis edematosa, dermopanniculosis deformans, status protrusus cutis, and gynoid lipodystrophy, comprising administering via subcutaneous methods, a subcutaneous formulation consisting essentially of a long-acting beta-2 adrenergic receptor agonist and a subcutaneously acceptable excipient thereof, wherein the formulation decreases cellulite in the subject.

Areas of fat deposits on a subject, such as for example a human patient, for which the formulations described herein are useful include, but are not limited to, the inside region of the knees, the middle to upper area of the upper arm, including the tricep area, the submental area, including the area under the chin, for example the wattle (which is understood to refer to the fleshy fold of skin in the submental area of a patient), the abdomen, the hips, the inner thigh, the outer thigh, the buttocks, an upper arms region of the patient, the lower back and the chest.

In some embodiments, inducing lipolysis and inhibiting fat cell growth in regional fat accumulations, have additional health benefits through the shrinkage of the average fat cell diameter or volume. Large volume fat cells actively secrete pro-inflammatory and deleterious hormones such as TNF-alpha and interleukins ("adipokines"), which contribute to comorbidities associated with fat, such as diabetes. By reducing the size of these fat cells and therefore the deleterious adipokine secretion, improvements in fat-related comorbidities are realized.

In some embodiments, the disclosed formulations (e.g., subcutaneous and transcutaneous formulations), are used for treating obstructive sleep apnea. Obstructive sleep apnea occurs when the airway is temporarily blocked during sleep, leading to hypoxia, high blood pressure, cardiac dysrhythmia, and a higher risk of death. Excessive fat in the pharynx and soft palate it believed to contribute to this blockage. Obese people have a higher incidence of sleep disorders and persons with sleep apnea have excessive fat in the palate and pharynx on MRI. Thus, in some embodiments, formulations described are administered to a subject to reduce the symptoms of sleep apnea. In some embodiments, the formulations are administered locally (e.g., by injection) into the palate or pharynx transorally. In some embodiments, the formulations are administered by subcutaneous into the region the neck to reduce the obstructive symptoms.

While certain embodiments have been described, these embodiments have been presented by way of example only, and are not intended to limit the scope of the disclosure. The formulations, methods, and systems described herein may be embodied in a variety of other forms. Furthermore, various omissions, substitutions and changes in the form of the formulations, methods, and systems described herein may be made without departing from the spirit of this disclosure. The accompanying claims and their equivalents are intended to cover such forms or modifications.

EXAMPLES

The following specific examples are to be construed as merely illustrative, and not limitative of the remainder of the disclosure in any way whatsoever. The examples described herein reference and provide non-limiting support to the various embodiments described in the preceding sections.

Example 1

Plasma Pharmacokinetics Following Single Intravenous and Subcutaneous Injections of a Lipophilic Long-Acting Selective Beta Agonist Materials and Methods: Salmeterol xinafoate was formulated in 5% PEG-400 in 0.9% saline, USP, at concentrations of 0.1, 1, 10, and 100 µg/mL. 1 male and 1 female non-naive Gottingen minipigs (18.4 to 19.5 kg at the time of the IV dose) were utilized. The animals were housed individually. The dosing scheme is shown in Table 1 below:

| Injection # | Route | Dose (µg/kg) | No. Animals |
|---|---|---|---|
| 1 | IV | 4 | 1 |
| 2 | SC | 4 | 1 |
| 3 | SC* | 4 | 1 |
| 4 | SC* | 0.004 | 1 |
| 5 | SC* | 0.04 | 1 |
| 6 | SC* | 0.4 | 1 |

*The dose volume was equally divided over 5 injection sites

Each minipig received a single IV injection followed by SC doses of the salmeterol formulation. The IV dose was administered by slow bolus (1 minute; 0.0167 hr) into the marginal ear vein, whereas the first SC dose was administered as a bolus injection along the back (neck-region) where there was a longitudinal fat depot. The second SC dose was distributed in 5 separate SC injection sites. The fourth, fifth, and sixth administrations were SC administrations divided over 5 injection sits of different graded concentrations (0.1, 1, and 10 µg/mL of salmeterol in 5% PEG). Each dose was separated by at least a 3-day washout period. Blood samples (approximately 4 mL) were collected via the branchiocephalic plexus at pre-dose and at 2.00, 5.00, 10.0, 20.0, 30.0 and 45.0 minutes, and at 1.00, 2.00, 4.00, 8.00 and 24.0 hr post-dose. Blood samples were placed in tubes containing $K_2$-EDTA as the anticoagulant. Samples were processed to plasma by centrifugation and stored frozen at approximately −70° C. (+/−15° C.) until shipment for analysis.

Sample Analysis: Plasma samples were analyzed for salmeterol using a qualified liquid chromatography/mass spectrometry/mass spectrometry (LC/MS/MS) method. The lower limit of quantitation (LLOQ) was 2.50 pg/mL. Samples were analyzed within a maximum of 14.0 days of collection.

Data Analysis: Non-compartmental pharmacokinetic parameters were calculated using WinNonlin 5.2 software, NCA model 202, IV infusion input for the IV data and NCA model 200, extravascular input for the SC data. Individual plasma concentrations for each animal were used in the calculation of pharmacokinetic parameters. Nominal collection times and doses were used in the calculations. The area under the plasma concentration-time curve (AUC) was calculated using linear trapezoidal approximation (linear/log interpolation). Concentration values below the assay limit of quantitation were set to zero for calculations. The maximum plasma concentration ($C_{max}$) and the time of its occurrence ($T_{max}$) were verified by inspection. The half-life ($t_{1/2}$) values were calculated using the last 3 plasma concentrations with nonzero values, if data permitted.

Results: The pharmacokinetic parameters are shown in Table 2. The plasma concentrations of salmeterol are shown in Table 3. The plasma concentrations of salmeterol and formoterol (via subcutaneous and intravenous administration) are shown in FIG. 1. Actual sampling times differed from nominal sampling times on occasion by more than 10%. Data in the apparent elimination phase were inadequate to calculate some pharmacokinetic parameters for some animals (indicated as ND for not determined or NA for not applicable). Bioavailability was likely poorly estimated due to scarcity of data in the apparent terminal elimination phase to calculate the apparent terminal elimination rate constant. This affected calculation of $AUC_{inf}$, $t_{1/2}$, CL, $V_{ss}$, and F. These departures are not believed to have significantly impacted the overall pharmacokinetic conclusions.

TABLE 2

Pharmacokinetic Parameters of Salmeterol Following IV and SC Administration to Gottingen Minipigs

| Route | Sex | Animal | $T_{max}$ (hr) | $C_{max}$ (Pg/mL) | $AUC_{inf}$ (pg · hr/mL) | $t_{1/2}$ (hr) | $t_{last}$ (hr) | CL (mL/hr/kg) | $V_{ss}$ (mL/kg) |
|---|---|---|---|---|---|---|---|---|---|
| IV | Female | 2-0623 | 0.0333 | 4950 | 1470 | 9.52 | 24.0 | 2730 | 22100 |
| IV | Male | 1-0771 | 0.0333 | 4290 | 1750 | 7.89 | 24.0 | 2280 | 17100 |
| SC1 4 | Female | 2-0623 | 1.00 | 403 | 1850 | 6.02 | 24.0 | 1.26 | |
| SC5 4 | Female | 2-0623 | 0.0333 | 626 | 2010 | 8.58 | 24.0 | 1.37 | |
| SC1 4 | Male | 1-0771 | 0.0833 | 575 | 1290 | 5.92 | 24.0 | 0.737 | |
| SC5 4 | Male | 1-0771 | 0.0833 | 681 | 1510 | 6.84 | 24.0 | 0.863 | |
| SC5 0.004 | Female | 2-0623 | 1.00 | 3.08 | ND | ND | 1.00 | ND | |
| SC5 0.004 | Male | 1-0771 | NA | 0 | ND | ND | NA | ND | |
| SC5 0.04 | Female | 2-0623 | 0.0333 | 8.31 | ND | ND | 0.0833 | ND | |
| SC5 0.04 | Male | 1-0771 | 0.0833 | 2.77 | ND | ND | 0.0833 | ND | |
| SC5 0.4 | Female | 2-0623 | 0.0333 | 113 | 164 | 2.88 | 8.00 | 1.12 | |
| SC5 0.4 | Male | 1-0771 | 0.0833 | 64.5 | 138 | 2.94 | 8.00 | 0.789 | |

$AUC_{inf}$ = area under the curve at infinite time.
CL = plasma clearance.
F = bioavailability;
NA = not applicable;
ND = not determined;
SC1—single site injection;
SC5 = SC injection split among 5 sites.
$t_{last}$ = time of last measurable plasma concentration.
$V_{ss}$ = volume of distribution at steady state
The IV dose was 4 μg/kg
The injection 4 SC5 0.004 μg/kg male showed no plasma concentrations >LLOQ of salmeterol at any time point.

TABLE 3

Plasma Concentrations of Salmeterol Following IV and SC Administration to Gottingen Minipigs (08-529)

| | | Dose | | | | | | Time (hr) | | | | | | |
|---|---|---|---|---|---|---|---|---|---|---|---|---|---|---|
| Inj | Rte | (mg/kg) | Sx | 0 | 0.0333 | 0.0833 | 0.167 | 0.333 | 0.500 | 0.750 | 1.00 | 2.00 | 4.00 | 8.00 | 24.0 |
| 1 | IV | 4 | M | < | 4290 | 1380 | 502 | 326 | 240 | 177 | 161 | 121 | 70.6 | 53.6 | 12.5 |
| 1 | IV | 4 | F | < | 4950 | 1300 | 559 | 322 | 232 | 152 | 154 | 81.1 | 49.1 | 35.3 | 11.3 |
| 2 | SC | 4 | M | < | 495 | 575 | 423 | 284 | 278 | 236 | 212 | 168 | 74.5 | 30.6 | 6.23 |
| 2 | SC | 4 | F | < | 124 | 227 | 206 | 334 | 302 | 351 | 403 | 206 | 108 | 54.4 | 10.0 |
| 3 | SC5 | 4 | M | < | 604 | 681 | 519 | 449 | 483 | 278 | 251 | 148 | 75.6 | 36.1 | 8.92 |
| 3 | SC5 | 4 | F | < | 626 | 485 | 442 | 398 | 435 | 435 | 388 | 196 | 86.8 | 51.0 | 16.1 |
| 4 | SC5 | 0.004 | M | < | < | < | < | < | < | < | < | < | < | < | < |
| 4 | SC5 | 0.004 | F | < | < | < | < | < | < | < | 3.08 | < | < | < | < |
| 5 | SC5 | 0.04 | M | < | < | 2.77 | < | < | < | < | < | < | < | < | < |
| 5 | SC5 | 0.04 | F | < | 8.31 | 3.17 | < | < | < | < | < | < | < | < | < |

TABLE 3-continued

Plasma Concentrations of Salmeterol Following IV and SC Administration to Gottingen Minipigs (08-529)

| | | Dose | | Time (hr) | | | | | | | | | | |
|---|---|---|---|---|---|---|---|---|---|---|---|---|---|---|
| Inj | Rte | (mg/kg) | Sx | 0 | 0.0333 | 0.0833 | 0.167 | 0.333 | 0.500 | 0.750 | 1.00 | 2.00 | 4.00 | 8.00 | 24.0 |
| 6 | SC5 | 0.4 | M | < | 32.0 | 64.5 | 57.0 | 43.3 | 53.8 | 26.5 | 28.7 | 19.5 | 8.46 | 4.41 | < |
| 6 | SC5 | 0.4 | F | < | 113 | 55.4 | 42.9 | 59.8 | 83.5 | 34.5 | 32.2 | 24.5 | 8.58 | 5.15 | < |

Plasma concentrations are reported in pg/mL.
LLOQ = 2.50 pg/mL.
< = LLOQ;
F = female;
Inj = Injection number;
M = male;
Rte = route;
SC1 = single site injection;
SC5 = SC injection split among 5 sites;
Sx = sex.
The male animal was number 1-0771 and the female animal number was number 2-0623

Overall there were no consistent, substantial differences in $C_{max}$ or $AUC_{inf}$ values between the male and female animal. Additionally, there was not a substantial difference in $C_{max}$ and $AUC_{inf}$ values between single site SC doses and multiple (5) site SC doses at the 4 µg/kg dose. The ratios (SC1/SC5) ranged from 0.644 to 0.844 for $C_{max}$ and 0.854 and 0.920 for $AUC_{inf}$. Salmeterol appeared to be well absorbed after SC administration at a single site at 4 µg/kg and after divided SC administration at 5 sites at the 4 and 0.4 µg/kg doses; bioavailability ranged from 0.737 to 0.863 for the male and 1.26 to 1.37 for the female for the 4 µg/kg dose regardless of the number of sites of administration and 0.789 for the male and 1.12 for the female for the 0.4 µg/kg dose at 5 divided SC sites. Scarce or no plasma concentrations were observed for the 0.04 and 0.004 divided SC doses.

Conclusion: In this single male and female Gottingen minipig study, salmeterol appeared to be well absorbed after subcutaneous administration at a single site and after divided SC administration at 5 sites at the 4 µg/kg dose and after divided SC administration of the 0.4 µg/kg dose. Overall there were no consistent, substantial differences in $C_{max}$ and $AUC_{inf}$ values between single site SC doses vs. multiple site SC doses. Overall there were no substantial differences in pharmacokinetic parameters between the male and female animals.

Example 2

Human Clinical Trial Comparing Lipophilic Long-acting Selective Beta-2 Adrenergic Receptor Agonists with Glucocorticosteroids, Their Combination, and Placebo

| | |
|---|---|
| Title | A Multi-center, Randomized, Double-Masked, Placebo-controlled, Multi-Factorial Evaluation of the Safety and Efficacy of a monotherapy lipophilic long-acting selective beta-2 adrenergic receptor agonist (e.g., salmeterol xinafoate (SX)) compared with a monotherapy glucocorticosteroid (e.g., fluticasone Propionate (FP)), a combination of FP and SX, and placebo for the Reduction of Subcutaneous Abdominal Adiposity |
| Study Objectives | This placebo-controlled factorial study examines the comparative efficacy and safety of SX alone, FP alone, and of the combination of SX + FP to reduce abdominal subcutaneous adipose tissue.<br>To evaluate the safety and efficacy of subcutaneous injections of 0.02 µg SX/mL once weekly for 8 weeks for the reduction of abdominal adiposity.<br>To evaluate the safety and efficacy of subcutaneous injections of 0.02 SX/mL once weekly for 8 weeks for the treatment of abdominal contour defects.<br>To evaluate the safety and efficacy of subcutaneous injections of 1.0 µg FP/mL once weekly for 8 weeks for the reduction of abdominal adiposity.<br>To evaluate the safety and efficacy of subcutaneous injections of SX + FP combo (1.0 µg FP + 0.02 µg SX/mL once weekly for 8 weeks) for the reduction of abdominal adiposity. |
| Study Design | A double-masked, multiple-dose study of the safety and efficacy of 0.02 µg/mL of SX alone compared to 1.0 µg/mL of FP alone, 1.0/0.02 µg/mL (FP/SX) combo, and to placebo. Doses will treat a region of adiposity and/or contour defect and will be administered as twenty 1 mL subcutaneous injections once a week for 8 weeks in 200 subjects with measurable abdominal subcutaneous adipose tissue. The total SX dose of 0.4 µg administered in 20 mL in this study is approx. 100 times lower than the established salmeterol dose that yields peak serum concentrations (Cmax) and systemic exposure (AUC) equivalent to the reference-listed product ADVAIR DISKUS ® 500/50. |
| Study Drug | SX is a sterile, preservative-free, clear, aqueous solution salmeterol xinafoate for injection. The drug products used in the study will be supplied as Salmeterol Xinafoate for Injection, 10 µg. A lyophile of the SX drug product will be supplied in separate 3 mL glass vials to be reconstituted with Sterile Water for Injection.<br>Immediately prior to administration, the lyophile drug products will be reconstituted and diluted with Sterile Saline Solution USP (0.9% Sodium Chloride). The supplied drug products (Salmeterol Xinafoate for Injection and Fluticasone Propionate for Injection) should be stored at room temperature (15° C. to 25° C.). The reconstituted |

| | |
|---|---|
| | solution of each drug product (the SX, FP, and combo) should be protected from light until administration.<br>The Salmeterol Xinafoate for Injection and Fluticasone Propionate for Injection drug products will be provided in bulk nested packaging.<br>Placebo: Sterile Saline, USP (0.9% Sodium Chloride) will be used as the placebo. |
| Treatment Groups | Eligible subjects in this multiple-dose study will be randomized into four groups of 50 to receive twenty 1 mL subcutaneous injections of either a combination of 1.0 µg/mL FP + 0.02 µg/mL SX, or 1.0 µg/mL FP alone, or 0.02 µg/mL SX alone, or Placebo. The 20 subcutaneous injections will be spaced approximately 4 cm apart and will treat a pre-marked abdominal area of adiposity that is approximately 400 cm$^2$.<br>The sequence of once weekly subcutaneous injections will continue for 8 consecutive weeks for a total of 160 injections administered into the marked abdominal area. Comprehensive safety assessments will be performed at each subject visit through the End of Study Visit on Day 78 ± 2 days. |
| Duration of Treatment | Screening period: up to 30 days.<br>The expected study duration is 12 weeks comprised of an 8 week treatment period and 1 and 4 week post-therapy follow-up visits for assessment of safety and efficacy. |
| Duration | Approx. 7 months |
| Study Population | The study population will consist of qualified male and female subjects, 18 years of age and older, inclusive who have provided written, informed consent. Qualified subjects, who meet all inclusion and exclusion criteria, will be enrolled into the study. |
| Total No. of Subjects | At least 200 subjects will be enrolled. The final subject number will be determined following an interim analysis to be conducted once 180 subjects have completed treatment or discontinued from the study. Subjects who give informed consent in writing but who do not receive study drug for any reason will be considered screen failures and will be replaced. |
| Sites | Up to 10 sites |
| Inclusion Criteria | 1) Healthy male and female patients, 18 years and older, who have provided written, informed consent prior to any study procedures (including pre-treatment and screening) being performed<br>2) Patients who have a localized area of abdominal subcutaneous adiposity, which is Grade 3 or higher on the Patient and Clinician Photonumeric Scales<br>3) Patients who have satisfactory abdominal skin elasticity as assessed by the investigator<br>4) BMI ≤ 25 kg/m2 and stable body weight as shown by a weight variance ≤ 3% between Screening and Day 1<br>5) History of a stable diet and exercise routine in the 3 months prior to Screening<br>6) Female subjects who have a negative urine pregnancy test at Screening and Day 1, and who agree to use adequate birth control methods (abstinence, female partner, stabilized on oral contraceptives for at least two months, implant, injection, IUD, patch, NuvaRing ®, condom and spermicidal, diaphragm and spermicidal) throughout the entire study until completion of the Week 12 End of Study Visit procedures |
| Exclusion Criteria | 1) History of prior treatment of abdominal subcutaneous adipose tissue (e.g., abdominoplasty, liposuction, or exposure to ablative or body contouring devices, mesotherapy or lipolytic agents)<br>2) Female subjects who are within 12 months post-partum, or who are pregnant, lactating, and/or who are of childbearing potential but not using adequate birth control methods<br>3) Any skin conditions in the treatment area that may affect study procedures or evaluations - including but not limited to skin infections, psoriasis, eczema, tattoos, striae, keloids, or hypertrophic or tethered scars, or excessive skin wrinkles, or a pannus<br>4) Subjects planning to embark on a weight loss or exercise program during study participation<br>5) Subjects who partake of abdominal massaging and who are unwilling to discontinue this therapy during the study<br>6) Known hypersensitivity to the study drugs and/or any of their components<br>7) Prior or current enrollment in any Lithera study involving SX, FP, or SX + FP.<br>8) Concurrent enrolment in another investigational drug or device study; or use of any experimental or investigational drug or device within 30 days, or for drugs within 6 times the elimination half-life prior to Day 1 if that is longer<br>9) Any medical condition that in the opinion of the investigator might jeopardize the subject's safety or complicate study procedures or assessments, including, but not limited to: (a) any bleeding, or connective tissue disorders; (b) asthma, COPD, diabetes (Type I and II) or cardiovascular disease (subjects with well-controlled hypertension will not be excluded unless they are taking beta-blocker drugs); (c) history of major surgery within 30 days prior to Day 1, or planned surgery during the study period; (d) any lymphatic disease causing lymphedema in the treatment area; (e) abdominal hernias, abdominal recti muscle divarication or diastasis, visible abdominal organomegaly, or abdominal asymmetry due to musculoskeletal abnormalities; (f) a history of any DSM-IV psychiatric disorder; (g) any clinically-significant physical examination findings, as determined by the Investigator, at Screening or Day 1; (h) any clinically-significant abnormal laboratory result during Screening and/or Day 1, as determined by the investigator |

| | |
|---|---|
| | 10) Use of drugs with anticoagulant activity (including aspirin and NSAIDs), immunomodulators (including steroids), anti-metabolites, β-adrenergic receptor agonists or blockers, strong CYP 3A inhibitors, or nonpotassium-sparing diuretics (e.g., loop or thiazide diuretics) prior to Day 1 during the study<br>11) Use of tricyclic antidepressants or monoamine oxidase inhibitor medications within 14 days prior to Day 1, or during the study<br>12) Subjects unlikely or unable to comply with protocol procedures or adhere to the study visit schedule |
| Procedures | All injections will be performed in an outpatient setting. At each visit, subjects will receive a total of 20 subcutaneous injections (1 mL) to infiltrate an area of approximately 400 $cm^2$. Subjects will maintain their usual diet and exercise routine during the study: any fat treatment, including but not limited to liposuction, mesotherapy and abdominal massaging will not be allowed.<br>Screening Procedures<br>Subjects will undergo screening procedures at the Screening Visit. This visit must occur within 30 days (Day −30 to Day 0) prior to study randomization at Day 1. Study procedures will be explained to each subject and written, informed consent must be obtained prior to initiating any study-related procedures, including screening procedures.<br>Qualified subjects, who meet all Inclusion/Exclusion criteria, with baseline screening laboratory tests results within normal limits as defined per protocol, will be scheduled for the Randomization Visit on Day 1.<br>It is required that all Randomization Visits (Day 1) are scheduled to ensure that over the 8 week treatment period, weekly study drug administration for each subject occurs in a regular cycle, with doses of study drug administered on the same day each week (±2 days).<br>On Study Procedures<br>Randomization and Treatment Visit (Day 1) Pre-dose (Day 1):<br>Eligible study subjects will visit the clinic on Day 1 and pre-dose procedures will be performed according to the Schedule of Events. For subjects continuing to meet all of the Inclusion/Exclusion criteria, baseline standardized digital photographs (using the Canfield Vectra ™ CR-10 16 mm 360° 3-D imaging system). Immediately thereafter, abdominal skin markings for the injection sites will be placed using the treatment area grid in order to ensure consistent study drug administration over the course of the study and a baseline abdominal circumferential measurement using a constant tension tape measure at pre-marked levels in the treatment area will be taken before dosing. Subjects then will be randomized to double-masked study drug. According to randomization, twenty 1.0 mL subcutaneous injections of either FP + SX, or 1.0 μg/mL FP alone, or 0.02 μg/mL SX alone, or Placebo will be administered into the abdominal treatment area using the injection grid.<br>Post-dose (Day 1):<br>After study drug administration, post-dose procedures will be performed according to the Schedule of Events. Subjects must remain in the clinic until the post-dose assessments have been completed and during this time concomitant medications and adverse events will be reviewed and recorded.<br>Before leaving the clinic, all subjects will be scheduled for their next visit. A subject will not be discharged from the clinic if, in the Investigator's opinion, the subject has an adverse event that requires further in-clinic monitoring.<br>Outpatient On-Treatment Visits (Days 8. 15. 22. 29. 36. 43. 50 ± 2):<br>Subjects will receive subcutaneous injections of study drug administered weekly for 8 weeks. At each study visit, 20 injections will be administered subcutaneously using a standard injection grid with the individual 1 mL injections being spaced approximately 4 cm apart. This schedule will be repeated for each subject for a total of 8 weekly treatment sessions during the study.<br>Pre-dose (Days 8. 15. 22. 29. 36. 43. 50 ± 2):<br>At each Treatment Visit, pre-dose procedures will be performed as per the Schedule of Events (TABLE 1).<br>Prior to study drug being injected on the dosing day of each week, circumferential tape measurements of the treatment area, at the pre-marked levels in the treatment area will be made. The skin markings on the abdomen will be used to align an injection grid that will be used to guide the administration of the injections on the assigned dosing day each week. The treatment area will be standardized, and will involve 20 individual subcutaneous injections at each treatment visit.<br>In addition, on Day 29 ± 2, a standardized measurement of the treatment area using a digital 3-D photographic device will be made prior to the application of the temporary injection grid.<br>Post-dose (Days 8, 15, 22, 29, 36, 43, 50 ± 2):<br>On all treatment visits, the post-dose procedures will be performed as per the Schedule of Events. Subjects must remain in the clinic until the post-dose assessments have been completed and during this time concomitant medications and adverse events will be reviewed and recorded. Before leaving the clinic, subjects will be scheduled for their next visit. A subject will not be discharged from the clinic if, in the Investigator's opinion, the subject has experienced an adverse event that requires further in-clinic monitoring.<br>1 Week Post-Treatment Visit (Day 57 ± 2):<br>A week after the last study drug administration on Day 57 ± 2, patients will return to the clinic for their initial post-treatment visit. The study procedures will be performed as per the Schedule of Events.<br>On Day 57 ± 2 a standardized measurement of the treatment area using 3-D photography will be performed. Then, abdominal circumference measurements using a tape measure at |

| | |
|---|---|
| | the pre-marked levels in the treatment area will be recorded.<br>Any abnormal laboratory tests that are clinically significant will be followed until resolution and/or repeated per protocol.<br>End of Study Visit (Day 78 ± 2) or Early Termination Visit:<br>Four weeks after the last study drug administration on Day 78 ± 2, patients will return to the clinic for their End of Study visit. The study procedures will be performed as per the Schedule of Events.<br>On Day 78 ± 2 a standardized measurement of the treatment area using 3-D photography will be performed. Then, abdominal circumference measurements using a tape measure at the pre-marked levels in the treatment area will be recorded.<br>If a subject withdraws from the study early, and the Day 78 ± 2 End of Study Visit procedures have not been performed, these procedures should be performed prior to terminating the subject from the study.<br>Any abnormal laboratory tests that are clinically significant will be followed until resolution and/or repeated per protocol. Once the End of Study Visit procedures have been performed, the subject has completed the study. |
| Safety Assessments | The following safety assessments will be performed at the designated time points as specified in the protocol: (1) vital signs (systolic and diastolic blood pressure, heart rate, breathing rate and body temperature); (2) physical examinations; (3) clinical assessment of injection site reactions (local tolerability using the Injection Site Reaction Severity Scale); (4) clinical laboratory tests (hematology, serum chemistry, and urine dipstick analysis); (5) adverse events.<br>Safety parameters monitored during this study will be compared within each treatment group (i.e. changes from baseline) and between treatment groups. |
| Efficacy Assessments | Efficacy assessments include: (1) circumferential measurements derived from analysis of standardized 3-D photographs of the treatment area; (2) manual tape circumferential measurement of the abdominal treatment area at the level of the umbilicus, and at other fixed levels in the treatment area; and, (3) volumetric changes in the treatment area derived from analysis of standardized 3-D photographs of the treatment area. |
| Study Endpoints | The study endpoints will include both safety assessments and evaluations of efficacy of the four treatments being assessed. The study population will be evaluated for several objective efficacy assessments based on standard measurements of subcutaneous adipose tissue during this study, including: (1) manual tape circumferential measurement of the abdominal treatment area at the level of the umbilicus, and at other fixed levels in the treatment area; (2) circumferential measurements derived from analysis of standardized 3-D photographs of the treatment area; and (3) volumetric changes in the treatment area derived from analysis of standardized 3-D photographs of the treatment area. |
| Sample Size Calc. | Initially 50 subjects per treatment group (total N = 200) with observable abdominal subcutaneous adipose tissue (per the Inclusion Criteria) will be enrolled (and have signed an IC form and received at least one dose of study drug).<br>As the assumption of variability greatly affects the estimate for sample size, an interim review to assess the change from baseline in abdominal measurements will be conducted to assess the adequacy of the overall sample size relative to achieving the study objectives. After approximately 180 subjects have completed the study, an interim analysis of the primary efficacy results only will be conducted by an independent statistician. This analysis will be used only to confirm the adequacy of the planned sample size or to recommend enlarging the sample size to achieve adequate statistical power to detect the hypothesized difference between the SX, FP, and FP + SX treatment groups. If the re-estimate of the sample size results in a study size that is not practical to complete, Lithera will complete the study as originally designed (Shun et al., 2001). |
| Statistical Analysis | Descriptive statistical analyses will be presented for all efficacy and safety endpoints. Summary statistics will include counts and percentages for categorical variables and the number of subjects, mean, standard deviation (SD), median, minimum and maximum for continuous variables.<br>Continuous efficacy endpoints will be summarized by treatment group using descriptive statistics. Differences between treatment groups will be assessed using an ANCOVA with effects for treatment, site, and baseline. |
| Compliance Statement | This protocol was developed according to the guidelines of the International Conference on<br>Harmonisation (ICH) Good Clinical Practice (GCP) Guidelines E6 and 21 Code of Federal |

Example 3

Pharmaceutical and Cosmetic Formulations

Subcutaneous Formulation

To prepare a parenteral pharmaceutical and/or cosmetic composition suitable for subcutaneous administration, a lipophilic, selective, long-acting beta agonist, such as salmeterol xinafoate, is dissolved in PEG 400 which is stabilized with polysorbate 80. Water is then added. This solution is stored in a single-use glass vial which is stored frozen and protected from light until dose preparation. When ready for use, the salmeterol solution is then diluted to a suitable concentration for subcutaneous administration using a diluent made of an aqueous solution of 20% PEG 400, 1% polysorbate 80, and sterile water for injection. Optionally, in certain embodiments, a co-solvent is used. In other embodiments, a co-solvent is not used. For example, in certain embodiments, a lipophilic, selective, long-acting beta agonist is lyophilized.

Transcutaneous Formulation

Also provided herein is a transcutaneous formulation for administration to a patient, and methods of treatment provided herein, including for example methods for the reduction of adipose tissue, using the transcutaneous formulations provided herein. In some embodiments, a lipophilic, selective, long-acting beta agonist is formulated in a transcutaneous formulation which comprises about 0.5% to about 10% by weight salmeterol xinafoate or formoterol fumarate, about 1% to about 75% propylene glycol or isopropyl alcohol, and optionally other excipients including but not limited to transcutol, propyl gallate, water, and ethanol, wherein the total percent by weight is 100%.

Example 4

Clinical Testing for Treatment of Graves' Ophthalmopathy with Compositions Comprising a Lipophilic Long-Acting Selective Beta Agonist A non-limiting example of such a clinical testing for treatment of Graves' Ophthalmopathy is as follows:

Patient Selection:

Patients are to be 18 years of age or above and have no hypersensitivity to the administered drugs. They are diagnosed with proptosis symptoms associated with Graves' Ophthalmopathy by ultrasonography or computerized tomography. In particular, patients are chosen with unilateral or bilateral proptosis edema of 3 mm or more, with or without eyelid swelling. Patients may also exhibit diplopia, limitation of eye movement in extreme positions, and evident restriction of movement. Patients may have undergone thyroidectomy for hyperthyroidism. Other steroid therapies should be not used for treatment of hyperthyroidism. All studies are to be performed with institutional ethics committee approval and patient consent.

Study Design:

Test 1: This is a multicenter, dose escalation study of the therapy of salmeterol, a long acting beta 2 agonist in the treatment of thyroid eye disease. Patients receive an injection administration of a parenteral composition of the drug daily. Patients who do not achieve proptosis improvement or partial or complete response but who have stable disease after 1 week of therapy will receive an additional 1 week of therapy at a higher dose than what is originally assigned. Cohorts of 3-6 patients receive escalating doses of the drug until the maximum tolerated dose (MTD) is determined. The MTD is defined as the dose preceding that at which 2 of 3 or 2 of 6 patients experience dose-limiting toxicity.

Test 2: This is a randomized, multicenter study. The study length is 60 days. Patients are randomized to 1 of 18 treatment groups. For group 1, patients are given salmeterol alone daily at MTD. For Group 2, patients are given salmeterol on every other day. For Group 3, patients are given salmeterol once a week. Groups 4-6 have the same dosing regime as 1-3 except the dosage is at one-fourth MTD. Groups 7-9 also have the same dosing regime as 1-3 except the dosage is at one-tenth MTD. In addition to the treatment groups, a control group is left untreated.

Endpoint Assessment:

Patients are assessed for reduction of proptosis and decrease of orbital fat volume and extraocular muscles at the conclusion of the study. Improvement in eyelid closure and ocular movement is also assessed. A 20% reduction within 60 days is presumed as a positive outcome.

Example 5

Testing for Aesthetic Treatment of Cheek Contour Defects with Compositions Comprising a Lipophilic Long-Acting Selective Beta Agonist A non-limiting example of such a clinical testing for aesthetic treatment of cheek contour defects is as follows:

Patient Selection:

Patients are to be 18 years of age or above and have no hypersensitivity to the administered drugs. Other steroid therapies should be not used. All studies are to be performed with institutional ethics committee approval and patient consent.

Study Design:

Test 1: This is a multicenter, dose escalation study of the therapy of salmeterol, a long acting beta 2 agonist in the aesthetic treatment of cheek contour defects. Patients receive an injection administration of a parenteral composition of the drug daily. Patients who do not achieve reduction of buccal or subcutaneous cheek fat after 1 week of therapy will receive an additional 1 week of therapy at a higher dose than what is originally assigned. Cohorts of 3-6 patients receive escalating doses of the drug until the maximum tolerated dose (MTD) is determined. The MTD is defined as the dose preceding that at which 2 of 3 or 2 of 6 patients experience dose-limiting toxicity.

Test 2: This is a randomized, multicenter study. The study length is 60 days. Patients are randomized to 1 of 18 treatment groups. For group 1, patients are given salmeterol alone daily at MTD. For Group 2, patients are given salmeterol on every other day. For Group 3, patients are given salmeterol once a week. Groups 4-6 have the same dosing regime as 1-3 except the dosage is at one-fourth MTD. Groups 7-9 also have the same dosing regime as 1-3 except the dosage is at one-tenth MTD. In addition to the treatment groups, a control group is left untreated.

Endpoint Assessment:

Patients are assessed for reduction of subcutaneous cheek fat or decrease of buccal fat volume at the conclusion of the study.

Example 6

Effects of a Lipophilic Long-Acting Selective Beta Agonist when Injected Sc in the Rat Inguinal Fat Pad The effects of salmeterol xinafoate on the inguinal fat pad weight of rats were evaluated following their SC injection into the inguinal fat pad. Mature male Sprague-Dawley rats weighing approximately 500 g were lightly anesthetized with 4% isoflurane. Test article injections (drug vehicle, different doses of salmeterol xinafoate) were injected SC into the right inguinal fat pad in a volume of 0.4 mL. An equal volume of drug vehicle was injected into the left inguinal fat pad. Rats received an injection comprising doses of 0.1 μg, 1 μg, 10 μg, or 100 μg in each fat pad on 3 consecutive days. Approximately 24 hours after the last injection, rats were anesthetized, sacrificed and the right and left fat pads harvested and weighed. The change in fat pad weight (Right vs. Left) was calculated and expressed as a percent change in inguinal fat pad weight (% change IFP= (Right side−Left side)×100/Left side).

The injection of salmeterol xinafoate into the rat inguinal fat pad produced a dose-related reduction in fat pad weight (FIG. 1). Staining and histological evaluation of the tissue showed a reduction in fat cell number and size (data not shown).

Example 7

Effects of a Lipophilic Long-Acting Selective Beta Agonist on Subcutaneous Fat Thickness in Male and Female Yucatan Minipigs A study was conducted using 2D-ultrasound to determine the effects of subcutaneously administered salmeterol xinafoate (SX) at 0.05, 0.5 or 5 µg on subcutaneous fat thickness in male and female Yucatan minipigs. The study was composed of (a control and three treated groups) each consisting of 1 minipig/sex for a total of eight minipigs. Each minipig had 4 sites designated for ultrasound measurement; the sites were in a 4 cm square orientation along the scapular region. Of the 4 sites, one site served as an ultrasound control (fat at this site was measured using ultrasound, but the site was never injected), while the remaining 3 sites were handled as follows: for the control pigs, the 3 remaining sites received an injection of saline during the dosing cycle. In the treated groups, one site served as a saline control, and 2 sites were designated for injection of 0.05, 0.5 or 5 µg of salmeterol xinafoate. Injections were delivered twice per week at a total volume of 1 mL/injection site. Each dosing cycle was two weeks in duration. SX was formulated in a vehicle of 5% PEG400 and 0.25% Tween 80 in water for injection (WFI).

Ultrasound measurements were made at each treatment site prior to dose administration on each treatment day, approximately 3-4 days after the last injection of the dosing cycle, and on the day of necropsy. Body weights were collected on the day prior to first dosing and weekly thereafter.

Figure 2:
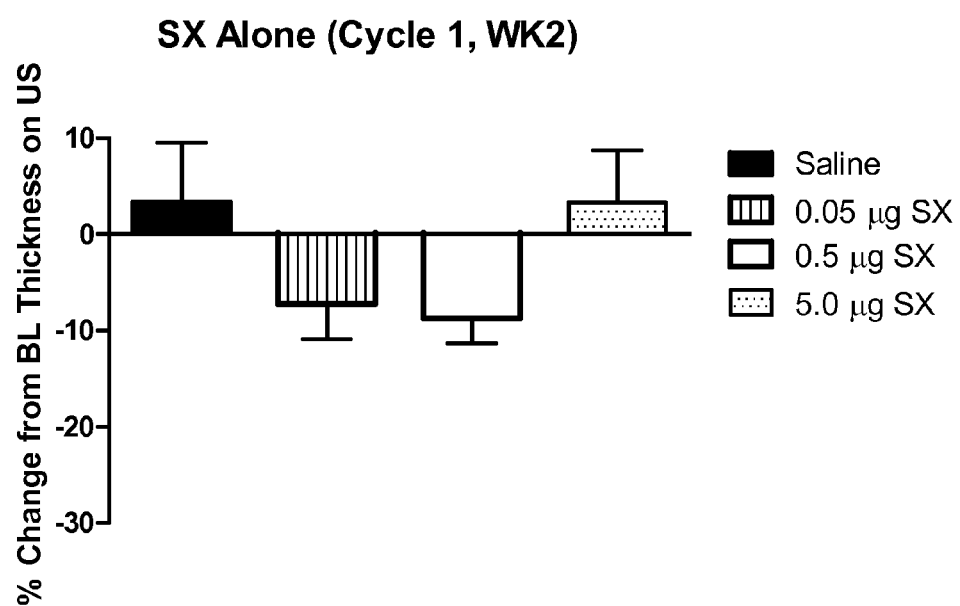
FIG. 2 shows effect of SC salmeterol xinafoate (SX) on change from baseline back fat thickness in Yucatan minipigs determined by 2D-ultrasound

Evaluation of the injection sites did not reveal any adverse reactions. Overall, all animals gained weight over the course of the study (body weight increases ranged from 3-7% in males and 6-12% in females). As seen in FIG. 2, administration of SX produced dose-related changes in fat thickness. The lowest doses of SX (0.05 and 0.5 ng) reduced total fat thickness by approximately 7-9%. The highest dose of SX (5 ng) increased fat thickness slightly (by approximately 3%), possibly due to β2-adrenergic receptor tachyphylaxis/desensitization at this dose and dosing schedule.

chiocephalic plexus at pre-dose and at 2, 5, 10, 20, 30, and 45 min, and at 1, 2, 4, 8, and 24 hr post-dose. Blood samples were placed in tubes containing K2-EDTA as the anticoagulant. Samples were processed to plasma by centrifugation under refrigeration and stored frozen at approximately −70° C. (±15° C.) until analysis.

Sample Analysis: Plasma samples were analyzed for salmeterol using qualified liquid chromatography/mass spectrometry/mass mass spectrometry (LC/MS/MS) methods. The lower limit of quantitation (LLOQ) was 2.50 pg/mL for salmeterol.

Data Analysis: Noncompartmental pharmacokinetic parameters were calculated using WinNonlin 5.2 software, NCA model 202, IV infusion input for the IV data and NCA model 200, extravascular input for the SC data (Pharsight Corporation, Mountain View, Calif.). Individual plasma concentrations for each animal were used in the calculation of pharmacokinetic parameters. Nominal collection times and doses were used in the calculations. The area under the plasma concentration-time curve (AUC) was calculated using linear trapezoidal approximation (linear/log interpolation). Concentration values below the assay limit of quantitation were set to zero for calculations. The maximum plasma concentration ($C_{max}$) and the time of its occurrence ($T_{max}$) were verified by inspection. The half-life (t½) values were calculated using the last 3 plasma concentrations with nonzero values, if data permitted. Other calculations were done using Microsoft Excel® XP. The bioanalytical and pharmacokinetic data were reported to 3 significant figures.

Results: The determined pharmacokinetic parameters are shown in Table 4 below.

TABLE 4

Pharmacokinetic parameters

| Analyte | Route | Dose (µg/kg) | Sex | $T_{max}$ (hr) | $C_{max}$ (pg/mL) | $AUC_{inf}$ (pg · hr/mL) | $t_{1/2}$ (hr) | $t_{last}$ (hr) | CL (mL/hr/kg) | $V_{ss}$ (mL/kg) | F |
|---|---|---|---|---|---|---|---|---|---|---|---|
| Salmeterol | SC | 4 | Fe | 0.500 | 433 | 1670 | 8.23 | 24.0 | NA | NA | NA |
| Salmeterol | SC | 4 | M | 0.333 | 564 | 2260 | 11.4 | 24.0 | NA | NA | NA |

$AUC_{inf}$ = area under the curve at infinite time,
CL = plasma clearance,
F = bioavailability,
Fe = female,
M = male,
NA = not applicable,
tlast = time of last measurable plasma concentration,
$V_{ss}$ = volume of distribution at steady state.
SC for fluticasone = single site SC injection,
SC for salmeterol xinafoate = single site SC injection.
Male = animal 1-0771,
female = animal 2-0623

Example 8

Study of Pharmacokinetics and Bioavailability of Lipophilic Long-Acting Selective Beta Agonist in Minipigs Plasma concentrations of salmeterol were monitored in a male and a female Gottingen minipig after SC administration of salmeterol xinafoate. SC dose of 4 µg/kg salmeterol xinafoate was administered as a single bolus dose. Each dose was separated by at least a 3-day washout period. Blood samples (approximately 4 mL) were collected via the bra- There were no apparent (consistent) gender differences in the SC PK of salmeterol xinafoate. Tmax values ranged from 0.333 to 0.5 hours, indicating that salmeterol xinafoate is rapidly absorbed following SC administration.

The examples and embodiments described herein are for illustrative purposes only and various modifications or changes are included within the spirit and purview of this application and scope of the appended claims. All publications, patents, and patent applications cited herein are hereby incorporated by reference for all purposes.

What is claimed is:

1. A method for treating a body contour defect by a monotherapy treatment regimen of at least about 4 weeks in duration, comprising subcutaneously administering a monotherapeutic formulation, wherein each administration during the monotherapy treatment regimen comprises the single active agent salmeterol, or a salt, solvate, or polymorph thereof that is present in an effective amount that is equal to or less than about 1 microgram per week, and wherein the formulation further consists of one or more subcutaneously acceptable inactive ingredients.

2. A cosmetic method for treating a body contour defect by a monotherapy treatment regimen of at least about 4 weeks in duration, comprising subcutaneously administering a monotherapeutic formulation, wherein each administration during the monotherapy treatment regimen comprises the single active agent salmeterol, or a salt, solvate, or polymorph thereof that is present in an effective amount that is equal to or less than about 1 microgram per week, and wherein the formulation further consists of one or more subcutaneously acceptable inactive ingredients.

3. A method for the aesthetic treatment of contour defects comprising abdominal bulging in a human patient by a monotherapy treatment regimen of at least about 4 weeks in duration, said method comprising subcutaneously administering a monotherapeutic formulation suitable for subcutaneous injection wherein the single active agent is salmeterol, or a salt, solvate, or polymorph thereof that is present in an effective amount that is equal to or less than about 1 microgram per week, and wherein the formulation further consists of one or more subcutaneously acceptable inactive ingredients.

4. The method of claim 1 wherein the lipophilic long-acting selective beta-2 adrenergic receptor agonist is salmeterol xinafoate.

5. The method of claim 4 wherein the formulation is formulated into a weekly dose of salmeterol xinafoate in an amount that is between about 12 nanograms to about 1 microgram.

6. The method of claim 1 wherein the salmeterol, or a salt, solvate, or polymorph thereof selectively partitions into adipose tissue relative to blood plasma when administered to a patient.

7. The method of claim 1 that provides a partition ratio of between about 0.01 to about 0.4 when salmeterol, or a salt, solvate, or polymorph thereof is administered subcutaneously.

8. The method of claim 1 wherein the injectable formulation is substantially free of glucocorticosteroids.

9. The method of claim 2 wherein the formulation is formulated to be administered to a patient once per week at a single session dose of salmeterol xinafoate that is equal to or less than about 1 microgram.

10. The method of claim 9 wherein the session dose is divided into at least two sub-doses of salmeterol xinafoate wherein each sub-dose is in an amount that is between about 12 nanograms to about 1 microgram.

11. The method of claim 2 wherein the formulation is administered to a patient once per week at a session dose of salmeterol xinafoate that is equal to or less than about 650 nanograms.

12. The method of claim 2 wherein the administration comprises at least one injection into a submental region of the patient, an abdominal region of the patient, a hip region of the patient, a thigh region of the patient, a buttocks region of the patient, a back region of the patient, an upper arms region of the patient, or a chest region of the patient.

13. The method of claim 3 wherein the lipophilic long-acting selective beta-2 adrenergic receptor agonist is salmeterol xinafoate.

14. The method of claim 13 wherein the formulation is formulated to be administered to a patient once per week at a single session dose of salmeterol xinafoate that is equal to or less than about 1 microgram.

15. The method of claim 14 wherein the session dose is divided into at least two sub-doses of salmeterol xinafoate wherein each sub-dose is in an amount that is between about 12 nanograms to about 1 microgram.

* * * * *